US010480925B2

(12) United States Patent
Walecki

(10) Patent No.: US 10,480,925 B2
(45) Date of Patent: Nov. 19, 2019

(54) INSPECTING A SLAB OF MATERIAL

(71) Applicant: Applejack 199 L.P., Milpitas, CA (US)

(72) Inventor: Wojciech Jan Walecki, Sunrise, FL (US)

(73) Assignee: APPLEJACK 199 L.P., Milpitas, CA (US)

(*) Notice: Subject to any disclaimer, the term of this patent is extended or adjusted under 35 U.S.C. 154(b) by 0 days.

(21) Appl. No.: 16/192,626

(22) Filed: Nov. 15, 2018

(65) Prior Publication Data
US 2019/0086191 A1 Mar. 21, 2019

Related U.S. Application Data

(63) Continuation-in-part of application No. 16/048,712, filed on Jul. 30, 2018, now Pat. No. 10,168,138, which is a continuation of application No. 15/919,003, filed on Mar. 12, 2018, now Pat. No. 10,036,624, which is a continuation-in-part of application No. 15/410,328, filed on Jan. 19, 2017, now Pat. No. 9,915,564.

(51) Int. Cl.
G01B 11/06 (2006.01)
G01B 9/02 (2006.01)
G01B 11/24 (2006.01)

(52) U.S. Cl.
CPC ...... *G01B 9/02011* (2013.01); *G01B 9/02007* (2013.01); *G01B 9/02025* (2013.01); *G01B 9/02044* (2013.01); *G01B 11/06* (2013.01); *G01B 11/2441* (2013.01); *G01B 2290/70* (2013.01)

(58) Field of Classification Search
CPC . G01B 11/06; G01B 11/0616; G01B 11/0675; G01B 9/0209; G01J 3/45
See application file for complete search history.

(56) References Cited

U.S. PATENT DOCUMENTS

| 5,357,340 | A | 10/1994 | Zochbauer |
| 5,946,095 | A | 8/1999 | Henningsen et al. |
| 7,084,985 | B2 | 8/2006 | Xie et al. |
| 9,915,564 | B1* | 3/2018 | Walecki ............ G01J 3/26 |
| 10,036,624 | B1 | 7/2018 | Walecki et al. |
| 10,113,860 | B1* | 10/2018 | Walecki ............ G01B 11/0675 |
| 2005/0264808 | A1* | 12/2005 | Wang ............ G01J 3/1256 356/328 |

(Continued)

*Primary Examiner* — Jonathan M Hansen
(74) *Attorney, Agent, or Firm* — Maschoff Brennan

(57) ABSTRACT

A system for inspecting a slab of material may include an optical fiber, a broadband light source configured to emit light having wavelengths of 780-1800 nanometers over the optical fiber, a beam-forming assembly configured to receive the light over the optical fiber and direct the light toward a slab of material, the beam-forming assembly may be configured to maintain the position of one or more elements within the beam-forming assembly despite changes in environmental temperature; a computer-controlled etalon filter configured to receive the light over the optical fiber, filter the light, and direct the light over the optical fiber; and a computer-controlled spectrometer configured to receive the light over the optical fiber after the light has been filtered by the etalon filter and after the light has been reflected from or transmitted through the slab of material and spectrally analyze the light.

15 Claims, 14 Drawing Sheets

(56) References Cited

U.S. PATENT DOCUMENTS

2010/0007894 A1* 1/2010 Suehira ............... A61B 3/1005
356/497
2017/0167919 A1 6/2017 Learmonth et al.

* cited by examiner

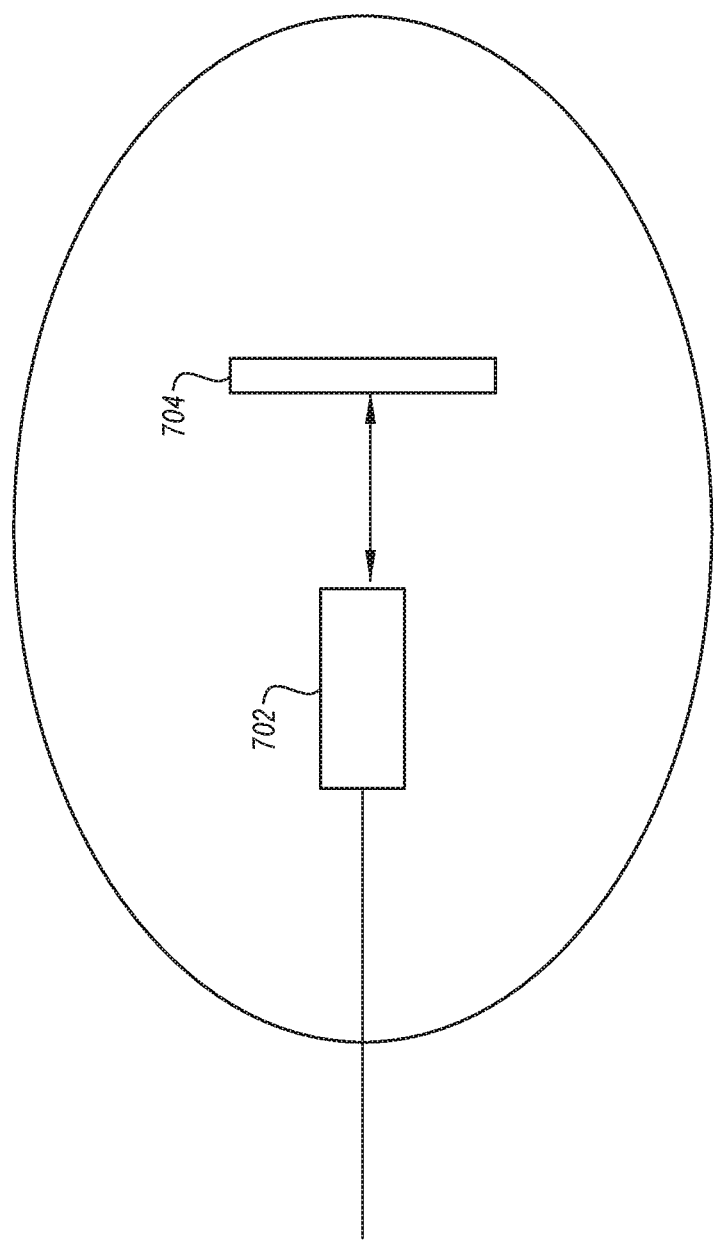

INSPECTING A SLAB OF MATERIAL

CROSS REFERENCE TO OTHER APPLICATION

This application is a continuation-in-part with respect to U.S. patent application Ser. No. 16/048,712 filed on Jul. 30, 2018 which is a continuation with respect to U.S. patent application Ser. No. 15/919,003 filed on Mar. 12, 2018, which is a continuation-in-part with respect to U.S. patent application Ser. No. 15/410,328 filed on Jan. 19, 2017.

FIELD

The embodiments discussed in this disclosure are related to systems and methods for inspecting a slab of material.

BACKGROUND

Thin slabs of material are often inspected to determine thickness using known methods of observation and analysis of Fabry Perot interference fringes. In the case of a simple single slab of material, these known methods of inspection are based on the observation of interference fringes in an etalon formed by the parallel interfaces of the sample.

Some of the commonly measured slabs of anisotropic materials such as sapphire are bi-refringent in nature and used as wafer-carriers. Birefringence of the substrate implies that speed with which light propagates through such slab depends on polarization state of the light. Sapphire-plates are commonly used as wafer carriers for GaAs (Gallium Arsenide) based wafers. Accordingly, an accurate determination of thickness of the sapphire plates may be required while measuring thickness of GaAs patterned wafers residing on the sapphire-carrier.

However, employment of conventional methods of determining the thickness of the slab of material may be substantially inaccurate with respect to the aforesaid anisotropic materials at least at least due to birefringence. Reasons for such inaccuracy in some instances may be based on the thickness of the slab of anisotropic material being greater than about 50 µm, measurement noise resulting from Schott noise, thermal noise, or the presence of stray light, or some combination thereof. Overall, the conventional methods for inspecting slab of material may not only have limited spectral-resolution, but may also not be effective when the slab of material to be measured exhibits birefringence and has the thickness as greater than 50 µm.

The subject matter claimed in this disclosure is not limited to embodiments that solve any disadvantages or that operate only in environments such as those described above. Rather, this background is only provided to illustrate one example technology area where some embodiments described in this disclosure may be practiced.

SUMMARY

According to an aspect of one or more embodiments, a system for inspecting a slab of material may include single mode optical fiber. The system may also include a broadband light source configured to emit light in a range from 780 nanometers (nm) to 1800 nm over the optical fiber. The system may also include a beam-forming assembly configured to receive the light over the optical fiber and direct the light toward a slab of material. The system may also include a computer-controlled etalon filter configured to receive the light over the optical fiber either before the light is directed toward the slab of material or after the light has been reflected from or transmitted through the slab of material, filter the light, and direct the light over the optical fiber. The system may also include a computer-controlled spectrometer configured to receive the light over the optical fiber after the light has been filtered by the etalon filter and after the light has been reflected from or transmitted through the slab of material and spectrally analyze the light.

According to an aspect of one or more embodiments, a system for inspecting a slab of material may include single mode optical fiber. The system may also include a broadband light source configured to emit light over the optical fiber and a beam-forming assembly. The beam-forming assembly may be configured to receive the light over the optical fiber. The beam-forming assembly may also be configured to split the light, at a beam splitter, into first and second portions after receiving the light over the optical fiber. The beam-forming assembly may also be configured to direct the first portion of the light toward the slab of material. The beam-forming assembly may also be configured to direct the second portion of the light onto a reflector that is maintained at a substantially constant distance from the beam splitter. The beam-forming assembly may also be configured to combine the first portion of the light after being reflected from the slab of material and the second portion of the light after being reflected from the reflector. The beam-forming assembly may also be configured to direct the combined light over the optical fiber. The system may also include a computer-controlled etalon filter configured to receive the light over the optical fiber either before the light is directed toward the slab of material or after the light has been reflected from or transmitted through the slab of material, filter the light, and direct the light over the optical fiber. The system may also include a computer-controlled spectrometer configured to receive the light over the optical fiber after the light has been filtered by the etalon filter and after the light has been reflected from or transmitted through the slab of material and spectrally analyze the light.

The objects and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which:

FIG. 7A illustrates an example etalon filter that may be employed in the system of FIG. 2;

DESCRIPTION OF EMBODIMENTS

According to at least one embodiment described in this disclosure, a system for inspecting a slab of material may be configured to determine a topography of one or more surfaces of the slab of material and/or determine a thickness of the slab of material. The material of the slab of material may be, for example, a semiconductor device such as any circuit, chip, or device that is fabricated on a silicon (Si) substrate wafer, a MEMS structure, or an interconnect feature used in 3D packaging. In some embodiments, the material of the slab material may be carriers for GaAs (gallium arsenide) wafers such as Sapphire plates that are anisotropic materials and that exhibit birefringence.

The system may include single mode optical fiber, a broadband light source, a beam-forming assembly, a computer-controlled etalon filter, and a computer-controlled spectrometer. The system may be employed to determine the thickness of a slab of material using only a single etalon, even when the thickness of the slab of material is greater than about 50 μm, resulting in a system having greater spectral resolution than known systems.

In these or other embodiments, the system may include a single mode polarization maintaining optical-fiber, a linearly polarized broadband light source, a beam-forming assembly, a polarization-rotator, a computer-controlled etalon filter, and a computer-controlled spectrometer. Either the etalon within the etalon filter or dispersive element within the spectrometer, or both, may be oriented at a pre-determined angle (e.g. Brewster angle) with respect to the incident-light or the polarized light received over the optical fiber. The system may be employed to determine the thickness of the slab of the anisotropic material exhibiting birefringence using only a single-etalon, even when the thickness of the slab is greater than about 50 μm, resulting in a system having greater spectral resolution than known systems and thereby a precise-determination of the thickness of the slab of the anisotropic material.

Embodiments of the present disclosure will be explained with reference to the accompanying drawings.

Figure 1A:
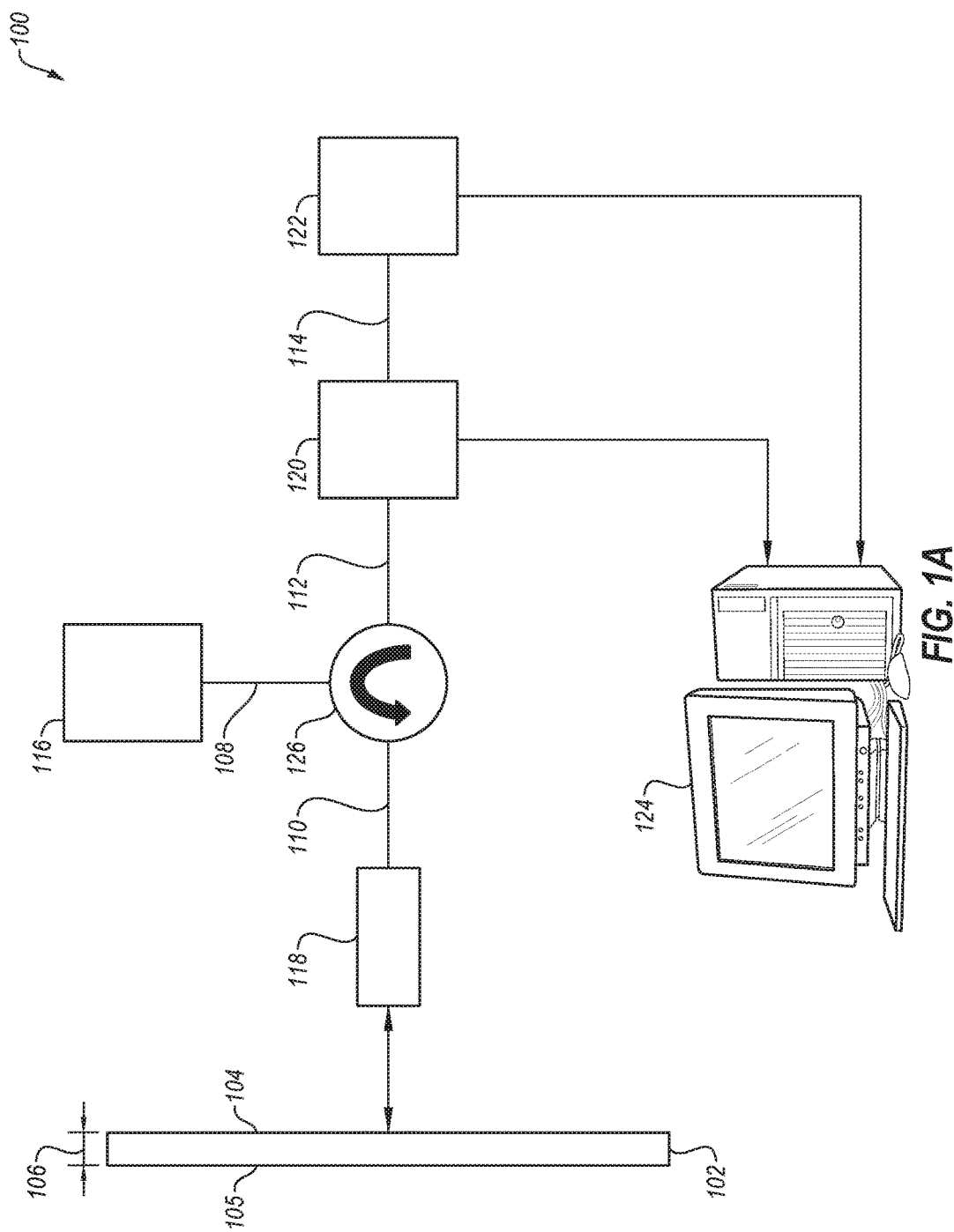
FIG. 1A illustrates a first example system for inspecting a slab of material.
Figure 1B:
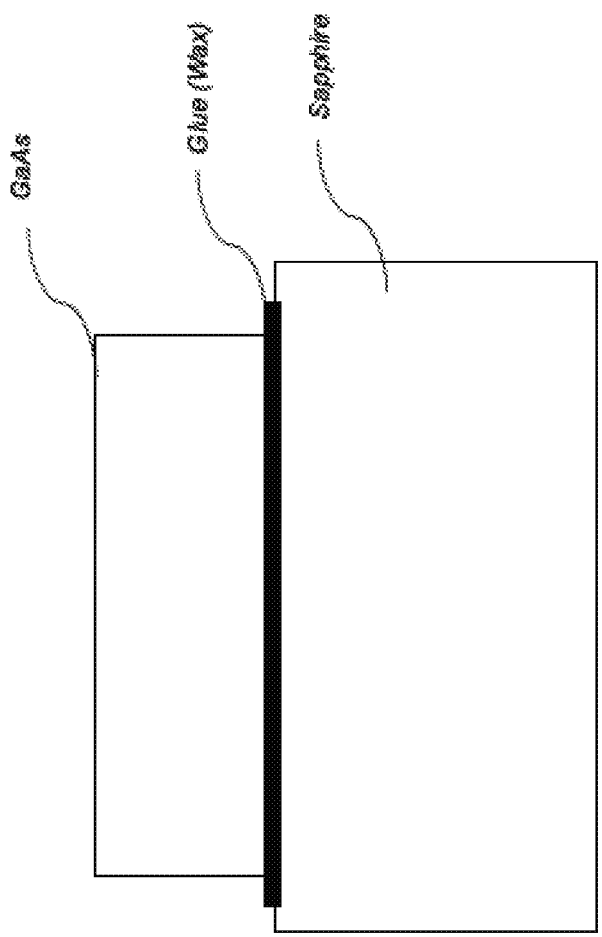
FIG. 1B illustrates an example semiconductor-wafer (e.g. GaAs) mounted on a wafer-carrier or substrate (e.g. sapphire plate)

FIG. 1A illustrates a first example system 100 for inspecting a slab of material 102, arranged in accordance with at least some embodiments described in this disclosure. Some of the commonly-measured slabs of materials such as sapphire-plates exhibit birefringence. Sapphire-plates are commonly used as wafer-carriers during processing of wafer of semiconductor-materials such as Gallium-Arsenide (GaAs) based wafers. In some embodiments, the system 100 may be configured to determine thickness of slabs of wafer-carriers exhibiting birefringence. As may be understood, birefringence of the substrate implies that speed with which light propagates through the slab depends on a polarization state of the light. For example, FIG. 1B illustrates an example semiconductor wafer of Gallium-Arsenide (GaAs) that may be supported on an example wafer-carrier such as a Sapphire Plate.

In general, the system 100 may be configured to inspect the slab of material 102 (which may include a slab of wafer-carriers such as sapphire-plates in some embodiments) in order to determine a topography of a front surface 104 and/or a back surface 105 of the slab of material 102 and/or in order to determine a thickness 106 of the slab of material 102. To perform the inspection, the system 100 may include single mode optical fibers 108, 110, 112, and 114 (which may be polarization maintaining in some embodiments), a broadband light source 116 (which may be linearly polarized in some embodiments), a beam-forming assembly 118, a directional element 126, a half-wave plate 119 acting as a polarization-rotator, an etalon-filter 120, and a spectrometer 122, wherein both the etalon-filter 120 and the spectrometer 122 are controlled by a computer 124.

The broadband light-source 116 may be configured to emit light over the optical-fiber 108. In some embodiments, the linearly polarized broadband light-source 116 may be configured to emit a linearly polarized light or plane-polarized light over the optical-fiber 108, such that a plane of polarization, i.e. the direction of polarization is pre-defined. The directional element 126 (e.g. an optical circulator) may be configured to receive the light from the broadband-light source 116 over the optical fiber 108 and direct the light to the beam forming assembly 118 over the optical fiber 110. In some embodiments, the light directed over the optical fiber 110 may be plane-polarized and the optical fiber 110 may be configured to maintain the polarization, such as indicated above.

In one the embodiment the broadband light source 116 may emit light in the wavelength range between 1100 nanometers (nm) and 1800 nm. The broadband light source may be implemented as a Superluminescent Light Emitter Device (SLED), such as Thorlabs part number SLD1325. The optical components including the optical fiber 108, the circulator 126, the optical fiber 110, the beam forming assembly 118, the optical fiber 112, the half wave plate 119, the etalon filter 120, the optical fiber 114, and the spectrometer 122 may be configured to operate in the same wavelength range as the light emitted by the broadband light source 116. The SLED may provide the advantage that emitted radiation can propagate without significant attenuation through Si and GaAs and may be used to probe layers of the semiconductor structures obscured by layer of Si, GaAs or similar material. Furthermore this according to Center for Device Radiological Health (CDRH) regulation, SLED is eye-safe as long as user-accessible light power does not exceed 1 milliwatt (mW).

In another embodiment, the broadband light source 116 may emit light in wavelength range of 780-1000 nm. The broadband light source 116 may be implemented as a SLED such as Thorlabs model SLD880S-A7. A broadband light source 116 that emits light in the wavelength range of 780-1000 nm may allow use of a spectrometer employing silicon-based detectors, which may be relatively inexpensive. Additionally or alternatively, Indium Gallium Arsenide (InGaAs) detectors may be used, such as, for example, in a system including a broadband light source that emits light in near-infrared wavelengths. The silicon-based detectors can be cooled or not cooled depending on desired signal-to-noise ratio for the entire system. In some embodiments silicon-based detectors operating in systems using visible light may be less noisy than infrared detectors having similar size and operating temperature.

The beam-forming assembly 118 may be configured to receive the light over the optical fiber 110 and direct the light toward the slab of material 102 in which the half-wave plate 119 may be omitted. Additionally or alternatively, the beam-assembly 118 may be configured to receive the light over the optical fiber 110 and direct the light towards the slab of material 102 via the half-wave plate 119 or any other known polarization rotator as known in the art. The half-wave plate 119 controls plane of polarization of light impinging the slab of material 102 by rotating the plane of polarization through a pre-defined angle. Overall, a pre-defined plane or direction of polarization as rendered by the linearly polarized broadband light source 116 as well as the controlled rotation of the plane of polarization as rendered by the half-wave plate 119 facilitates a constant polarization of the light within the slab of material 102.

The beam-assembly 118 may be further configured to receive the light reflected from the slab of material 102 and direct the light back to the directional element 126 over the optical fiber 110. The etalon filter 120, as controlled by the computer 124, may be configured to receive the light over the optical fiber 112 after the light has been reflected from the slab of material 102, filter the light, and direct the light over the optical fiber 114. The spectrometer 122, as controlled by the computer 124, may be configured to receive the light over the optical fiber 114, after the light has been filtered by the etalon filter 120 and after the light has been reflected from the slab of material 102, and spectrally analyze the light. The spectral analysis of the light may include determining a topography of the front surface 104 and/or the back surface 105 of the slab of material 102 and/or determining the thickness 106 of the slab of material 102.

Figure 6A:
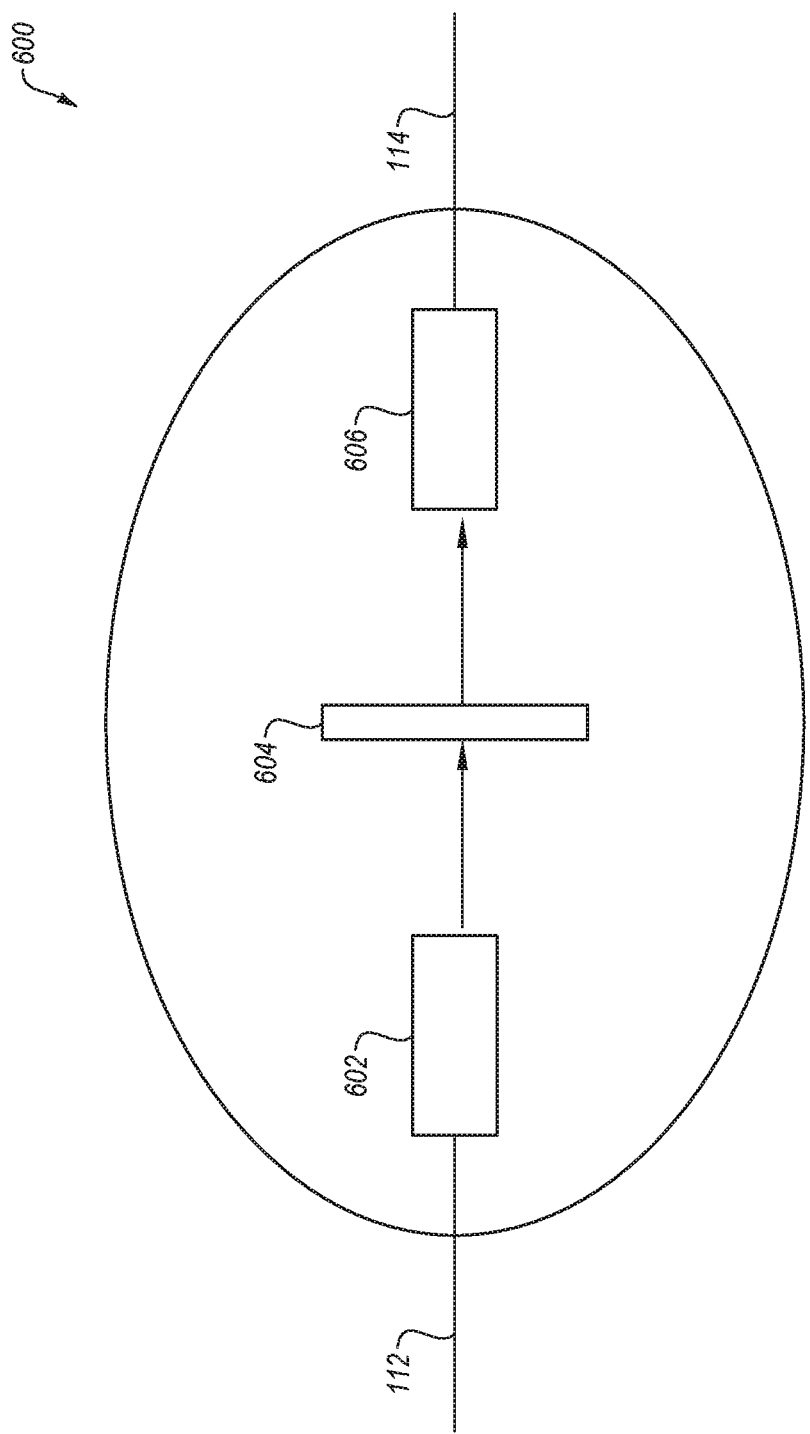
FIG. 6A illustrates an example etalon filter that may be employed in the systems of FIGS. 1, 3, and 4.
Figure 6B:
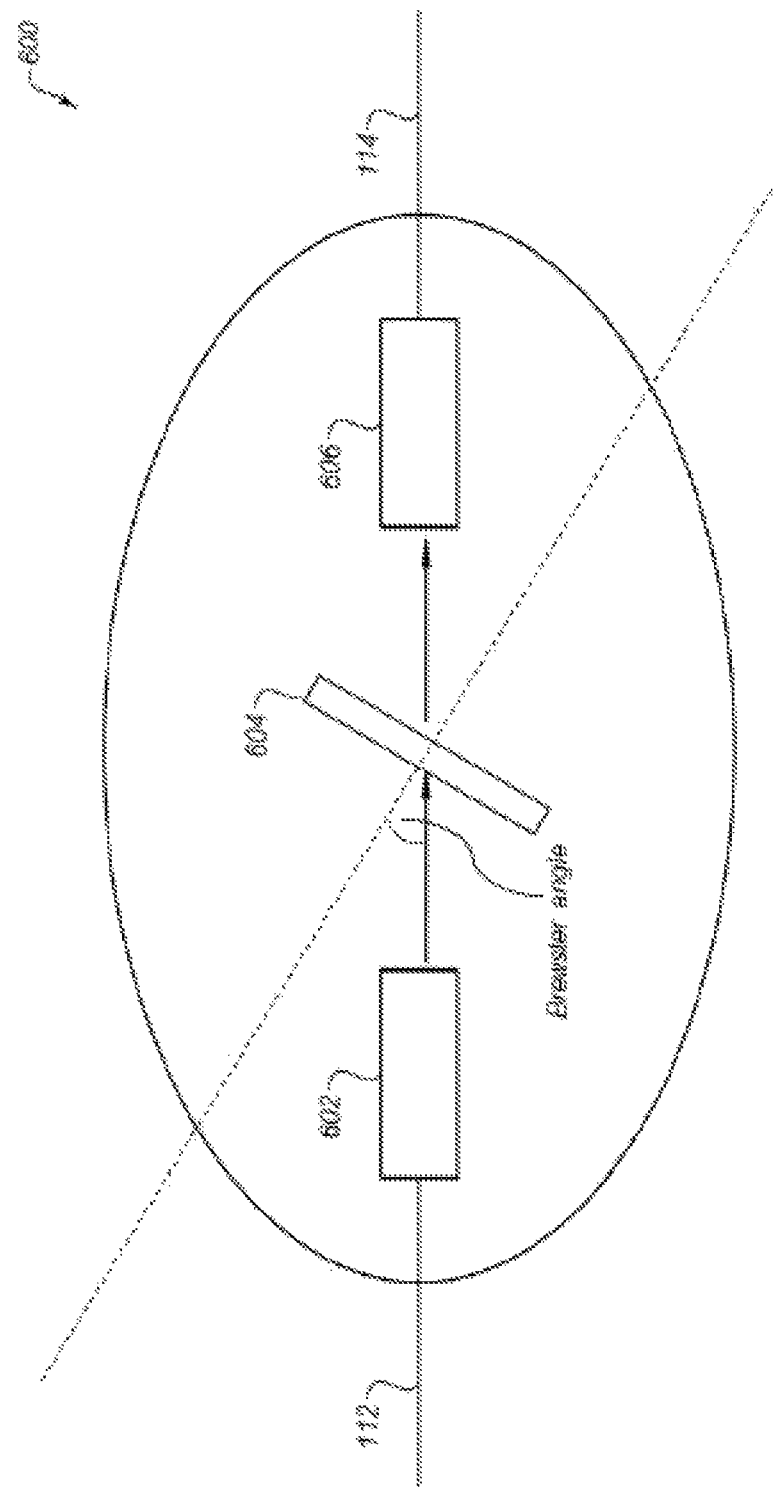
FIG. 6B illustrates an etalon operating at a Brewster-angle in FIG. 6A.
Figure 7B:
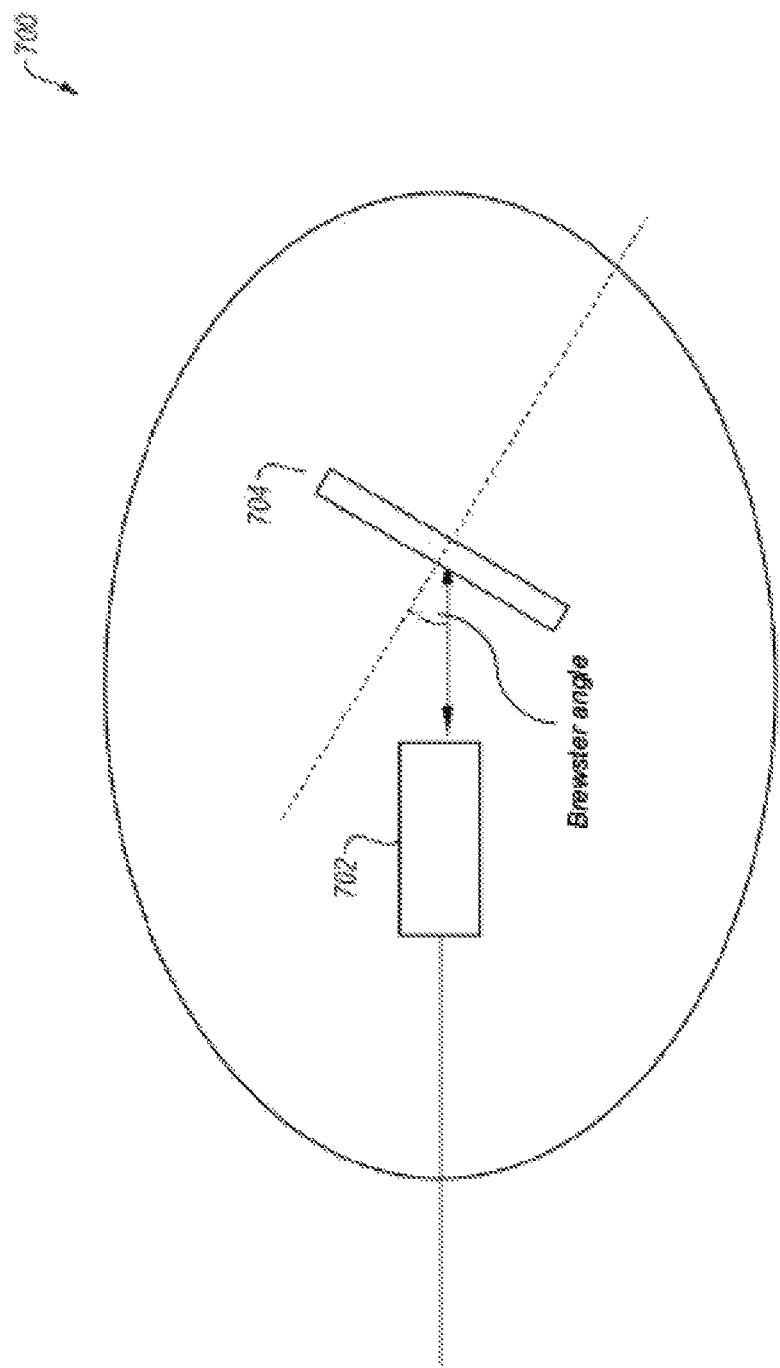
FIG. 7B illustrates an example etalon filter operating at a Brewster-angle in FIG. 7A.

In a some embodiments (e.g., instances in which the light is polarized), an etalon 604 or 704 (see FIG. 6 and FIG. 7) may be placed within the etalon filter 120 at a 'Brewster angle' with respect to the incident polarized light (as illustrated in FIG. 6B and FIG. 7B) in order to reduce or eliminate reflection of the polarized light from the front-surface of the etalon. In addition, in case the spectrometer 122 comprises grating as a dispersive element, then the efficiency of the grating may be improved or optimized by maintaining a specific-angle between grooves of the grating and the plane of polarization of the light incident upon the grating. In embodiments in which the spectrometer 122 includes a prism as the dispersive element, then the prism may be oriented with respect to the incident polarized light in a manner such that the light impinges the prism at the Brewster angle, thereby reducing or eliminating reflection loss on a first surface of the prism of the spectrometer.

The computer 124 may be electrically coupled to the etalon filter 120 and to spectrometer 122. In these and other embodiments, the computer 124 may be configured to determine a topography of the front surface 104 and/or the back surface 105 of the slab of material 102 and/or determine the thickness 106 of the slab of material 102. The computer 124 may include a processor and a memory. The processor may include, for example, a microprocessor, microcontroller, digital signal processor (DSP), application-specific integrated circuit (ASIC), a Field-Programmable Gate Array (FPGA), or any other digital or analog circuitry configured to interpret and/or to execute program instructions and/or to process data. In some embodiments, the processor may interpret and/or execute program instructions and/or process data stored in the memory. The processor may execute instructions to perform operations with respect to the spectrometer 122 in order to determine a topography of the front surface 104 and/or the back surface 105 of the slab of material 102 and/or determine the thickness 106 of the slab of material 102. The memory may include any suitable computer-readable media configured to retain program instructions and/or data for a period of time. By way of example, and not limitation, such computer-readable media may include tangible and/or non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable media. Computer-executable instructions may include, for example, instructions and data that cause a general-purpose computer, special-purpose computer, or special-purpose processing device to perform a certain function or group of functions.

The etalon filter 120 may be a fixed etalon filter or may be a tunable etalon filter. In principle, if the optical thickness of the etalon filter 120 is known, and if the slab of material 102 is placed at a perfectly normal direction to the light from the beam-forming assembly 118, the etalon filter 120 may be a fixed etalon filter and may not need calibration. However, if any of these conditions are not met, the etalon filter 120 may need to be a tunable etalon filter.

In one tunable embodiment, the etalon filter 120 may include multiple-etalons with each etalon including two parallel reflective surfaces and with each etalon mounted in a computer-controlled motorized wheel. In another tunable embodiment, the etalon filter 120 may include two parallel reflective surfaces with at least one of the two parallel reflective surfaces being mounted on a computer-controlled linear motion stage. In either of these tunable embodiments, the etalon filter 120 may be tunable in order to allow the optical thickness of the etalon filter to be similar to the thickness 106 of the particular slab of material 102 that is to be inspected by the system 100. For example, the etalon filter 120 may include two parallel reflective surfaces separated by a distance, which is the optical thickness of the etalon filter 120, and during calibration of the etalon filter 120 the distance may be adjusted so that the distance is within 250 microns of the thickness 106 of the slab of material 102.

This calibration may include placing a slab of material of a known refractive index n and known thickness t in the system 100 and measuring its apparent optical thickness of calibration standard (AOTCS). The result of the measurement is used to calculate a calibration factor CF given by CF=n*t/AOTCS. When measuring actual slabs of material, the optical thickness (OT) of the slabs of material is given by OT=CF*AOT, where AOT is the measured apparent optical thickness.

The system 100 may be advantageously employed when the optical thickness (OT) of the etalon filter 120 is similar to the thickness of the slab of material 102 to be inspected, such as within 250 microns of the slab of material 102 to be inspected. The system 100 may also be employed when interference happens between the front surface 104 of the slab of material 102 and a reflector 508 (see FIG. 5), enabling a topography of the front surface 104 and/or the back surface 105 of the slab of material 102 to be determined.

In the case of a single parallel plate forming a simple non-absorbing etalon, the reflection of the light propagating through a slab of material is given by the Equation:

$$R = \frac{F \sin(\delta/2)^2}{1 + F \sin(\delta/2)^2} \tag{1}$$

where the coefficient of finesse F is defined by the Equation:

$$F = \frac{4r}{(1-r)^2} \tag{2}$$

where r is a Fresnel reflection at the interfaces of the slab of material forming the etalon, and where the optical path difference $\delta$ is given by the Equation:

$$\delta = \frac{2\pi}{\lambda} 2nd \tag{3}$$

if one assumes that optical radiation having wavelength $\lambda$ propagates in the direction perpendicular to faces of the slab of material having refractive index n and thickness d. Since bandwidth of a light source is finite in this instance, for the sake of simplicity we may ignore spectral dispersion of the slab of material 102 and we may assume that the refractive index does not depend on the wavelength.

For a non-absorbing etalon, the law of conservation energy requires the following Equation:

$$T + R = 1 \tag{4}$$

And therefore, directly from Equations (1) and (3) above, we may derive the following Equation:

$$T = \frac{1}{1 + F \sin(\delta/2)^2} \tag{5}$$

The reflection and transmission given by Equations (1) and (5) reveal oscillations known as Fabry-Perot fringes. Directly from Equations (1) and (2) we see that spacing between fringes on such an etalon in the absence of the spectral dispersion (and sometimes referred to as free spectral range) is given by the Equation:

$$\Delta\lambda_{FSR} = \frac{\lambda^2}{2nd} \tag{6}$$

Or in frequency domain spacing between fringes is constant and equal to the Equation:

$$\Delta\upsilon_{FSR} = \frac{c}{2nd} \tag{7}$$

The intensity of the light reflected from the sample $I(\lambda)$ is given simply by product of the intensity of light emitted from a broadband light source (e.g., a linearly polarized broadband light source in some instances) $I_{source}(\lambda)$ and reflection of the sample $R(\lambda)$ given by Equation (1), according to the following Equation:

$$I(\lambda) = R(\lambda) \cdot I_{source}(\lambda) \tag{8}$$

Since the spectrum of the source may be measured independently, the measurement of the spectrum of reflected beam can be used to find reflection of the sample, according to the Equation:

$$R(\lambda) = \frac{I(\lambda)}{I_{source}(\lambda)} \tag{9}$$

When the reflection function is established from Equation (1), one can use the measurement of spacing between fringes or the frequency of observed fringes to establish the thickness of the slab of material according to the following Equation:

$$F = \frac{4r}{(1-r)^2} \tag{10}$$

The observed spectrum by spectrograph comprising a spectrometer and array detector are given by convolution of intensity spectrum impinging an entrance slit $I(\lambda)$ of the spectrometer and a response function of the spectrometer $\mathcal{R}(\lambda, \tilde{\lambda})$ according to the Equation:

$$I_{observed}(\lambda) = \int_0^\infty \mathcal{R}(\lambda, \tilde{\lambda}) \ast I(\tilde{\lambda}) d\tilde{\lambda} \tag{11}$$

The response function of the spectrometer can be modelled by a simple boxcar function:

$$\mathcal{R}(\lambda, \tilde{\lambda}) = \frac{\theta(\Delta\lambda/2 - |\lambda - \tilde{\lambda}|)}{\Delta\lambda} \tag{12}$$

where $\theta$ is a Heaviside step function, $\Delta\lambda$ is bandwidth of spectrograph, $\lambda$ is a wavelength measured by spectrograph, and $\tilde{\lambda}$ is wavelength of incoming radiation.

In this simplified model we have neglected additional broadening caused by finite pixel size, and aberration of the spectrometer.

In the case of the system 100 being employed when the optical thickness of the etalon filter 120 is similar to the thickness of the slab of material 102 to be inspected, the transmission of the reference may be given by the following Equation:

$$T_{ref} = \frac{1}{1 + F_{ref}\sin(\delta_{ref}/2)^2} \tag{13}$$

where finesse coefficient and optical path difference are defined just as in the case of our sample by the following Equations:

$$F_{ref} = \frac{4r_{ref}}{(1-r_{ref})^2} \text{ and} \qquad (14)$$

$$\delta_{ref} = \frac{2\pi}{\lambda} n_{ref} d_{ref} \qquad (15)$$

The intensity of light emitted by the broadband light source 116, reflected by the slab of material 102, and impinging a slit of the spectrometer 122, is given by:

$$I(\lambda) = T_{ref}(\lambda) \cdot R(\lambda) \cdot I_{source}(\lambda) \qquad (16)$$

or in frequency domain $$I(k) = T_{ref}(k) \cdot R(k) \cdot I_{source}(k) \qquad (17)$$

where k=1/λ and $$I_{observed}(k) = \int_0^\infty \mathcal{R}(k,\tilde{k}) * I(\tilde{k}) d\tilde{k} \qquad (18)$$

Since both R(λ) and $T_{ref}(\lambda)$ functions reveal narrow fringes of a similar period (since the reference etalon optical path difference (OPD) has been selected to be close to the sample OPD), their product will reveal oscillations corresponding to beats of the fringes in the sample and the reference etalon.

Origin of the observed beats can be understood using Fourier expansion of the R(k), and $T_{ref}(k)$, according to the following Equation:

$$R(k) = a_0 + \sum_{n=1}^\infty \left( a_n \cos\frac{n\pi k}{\Delta v_{FSR}} + b_n \sin\frac{n\pi k}{\Delta v_{FSR}} \right) \qquad (19)$$

where $a_0$, $a_n$, and $b_n$ are constants. Since R(k) is an even function we have $b_n = 0$ for all n. So R(k) is given by the Equation:

$$R(k) = a_0 + \sum_{n=1}^\infty a_n \cos\frac{n\pi k}{\Delta v_{FSR}} \qquad (20)$$

Similar argument for the $T_{ref}(k)$ leads to the following Equation:

$$T_{ref}(k) = a_{ref,0} + \sum_{n=1}^\infty a_{ref,n} \cos\frac{n\pi k}{\Delta v_{ref,FSR}} \qquad (21)$$

where $$\Delta v_{FSR} = \frac{c}{2n_{ref} d_{ref}} \qquad (22)$$

where $n_{ref}$ is refractive index of the reference etalon, and $d_{ref}$ is the thickness of the etalon.

Therefore, the product may be found in the following Equation:

$$R(k) \cdot T_{ref}(k) = \left( a_0 + \sum_{n=1}^\infty a_n \cos\frac{n\pi k}{\Delta v_{FSR}} \right)\left( a_{ref,0} + \sum_{m=1}^\infty a_{ref,m} \cos\frac{m\pi k}{\Delta v_{ref,FSR}} \right) \qquad (23)$$

By unfolding brackets, we get the following Equation:

$$R(k) \cdot T_{ref}(k) = a_0 a_{ref,0} + a_0 a_{ref,1}\cos\frac{1\pi k}{\Delta v_{ref,FSR}} + \qquad (24)$$
$$a_1 a_{ref,0}\cos\frac{1\pi k}{\Delta v_{FSR}} + a_1 a_{ref,1}\cos\frac{1\pi k}{\Delta v_{FSR}}\cos\frac{1\pi k}{\Delta v_{ref,FSR}} + \ldots$$

Then from the above we get the following Equation:

$$R(k) \cdot T_{ref}(k) = a_0 a_{ref,0} + a_0 a_{ref,1}\cos\frac{1\pi k}{\Delta v_{ref,FSR}} + \qquad (25)$$
$$a_1 a_{ref,0}\cos\frac{1\pi k}{\Delta v_{FSR}} + a_1 a_{ref,1}\cos\frac{1\pi k}{\Delta v_{FSR}}\cos\frac{1\pi k}{\Delta v_{ref,FSR}} + \ldots$$

Since the thicknesses of the reference etalon and the sample are similar, we can use the trigonometric Equation:

$$R(k) \cdot T_{ref}(k) = a_0 a_{ref,0} + a_0 a_{ref,1}\cos\frac{1\pi k}{\Delta v_{ref,FSR}} + \qquad (26)$$
$$a_1 a_{ref,0}\cos\frac{1\pi k}{\Delta v_{FSR}} + \frac{1}{2} a_1 a_{ref,1}\cos\left(\frac{1\pi k}{\Delta v_{ref}} - \frac{1\pi k}{\Delta v_{ref,FSR}}\right) +$$
$$\frac{1}{2} a_1 a_{ref,1}\cos\left(\frac{1\pi k}{\Delta v_{ref}} + \frac{1\pi k}{\Delta v_{ref,FSR}}\right) + \ldots$$

By substituting Equations (7) and (22) and rearranging terms, we get the Equation:

$$R(k) \cdot T_{ref}(k) = a_0 a_{ref,0} + \frac{1}{2} a_1 a_{ref,1}\cos\left(\frac{2\pi(n_{ref} d_{ref} - nd)k}{c}\right) + \qquad (27)$$
$$\frac{1}{2} a_1 a_{ref,1}\cos\left(\frac{2\pi(n_{ref} d_{ref} - nd)k}{c}\right) +$$
$$a_0 a_{ref,1}\cos\frac{1\pi k}{\Delta v_{ref,FSR}} + a_1 a_{ref,0}\cos\frac{1\pi k}{\Delta v_{FSR}} + \ldots$$

The first and the second terms are slow varying terms in comparison to $\Delta v_{FSR}$. Therefore, we can rewrite the above Equation as the Equation:

$$R(k) \cdot T_{ref}(k) = a_0 a_{ref,0} + \qquad (28)$$
$$\frac{1}{2} a_1 a_{ref,1}\cos\left(\frac{2\pi(n_{ref} d_{ref} - nd)k}{c}\right) + \text{rapidly varying terms in } k$$

Since the spectrograph response function is filtering out the rapidly varying terms, the observed signal has a form of the Equation:

$$I_{observed}(k) = \int_0^\infty \mathcal{R}(k,\tilde{k})(k) \cdot R(\tilde{k}) \cdot T_{ref}(\tilde{k}) \cdot I_{source}(\tilde{k}) d\tilde{k} \qquad (29)$$

Since the light source is broadband and has a slowly varying spectrum in function of k, we have the following Equations:

$$I_{observed}(k) = I_{source}(k) \int_0^\infty \mathcal{R}(k,\tilde{k}) \cdot R(\tilde{k}) \cdot T_{ref}(\tilde{k}) d\tilde{k} \qquad (30)$$

-continued $$I_{observed}(k) = \quad (31)$$
$$I_{source}(k) \int_0^\infty \mathcal{R}(k, \tilde{k}) \cdot \left[ a_0 a_{ref,0} + \frac{1}{2} a_1 a_{ref,1} \cos\left(\frac{2\pi(n_{ref} d_{ref} - nd)\tilde{k}}{c}\right) + \text{rapidly varying terms in } \tilde{k} \right] d\tilde{k}$$

Since the spectrograph response function does not affect slowly varying functions (because it acts as a smoothing filter), we get from above the Equation:

$$\frac{I_{observed}(k)}{I_{source}(k)} = a_0 a_{ref,0} + \quad (32)$$
$$\frac{1}{2} a_1 a_{ref,1} \cos\left(\frac{2\pi(n_{ref} d_{ref} - nd)k}{c}\right) + \text{rapidly varying terms in } k$$

The above equation can be used directly to measure the thickness of a relatively thick slab of material using the system 100 which employs the reference etalon filter 120. The system 100 may accomplish this measurement by measuring the spectrum of the broadband light source 116, measuring the spectrum of the light reflected from the slab of material 102, and transmitted through the reference etalon filter 120, calculating ratio $$\frac{I_{observed}(k)}{I_{source}(k)},$$

and finding experimentally the lowest non-zero angular frequency of the observed oscillations in function of k, according to the following Equation:

$$\Omega = \frac{2\pi|(n_{ref} d_{ref} - nd)|}{c} \quad (33)$$

Note that $\Omega$ may have a unit of time, since it is the frequency of the fringes observed in the frequency space.

If it is known that $(n_{ref}d_{ref}-nd)>0$, then the thickness of the slab of material 102 can be found directly from the Equation:

$$d = \frac{2\pi(n_{ref} d_{ref})}{n} - \Omega c \quad (34)$$

The value of $\Omega$ from measured ratio $$\frac{I_{observed}(k)}{I_{source}(k)}$$

can be found using standard numerical techniques including but not limited to techniques based on Fourier transforms.

If it is known that $(n_{ref}d_{ref}-nd)\leq 0$ then the thickness of the layer can be found directly from the Equation:

$$d = \Omega c - \frac{2\pi(n_{ref} d_{ref})}{n} \quad (35)$$

Any ambiguity resulting from the choice between Equations (34) and (35) can be facilitated by use of a plurality of reference etalons having different optical thicknesses $n_{ref}d_{ref}$, or by use of the same reference etalon at normal and at a tilted angle which would increase the optical path in the reference etalon.

Figure 9A:
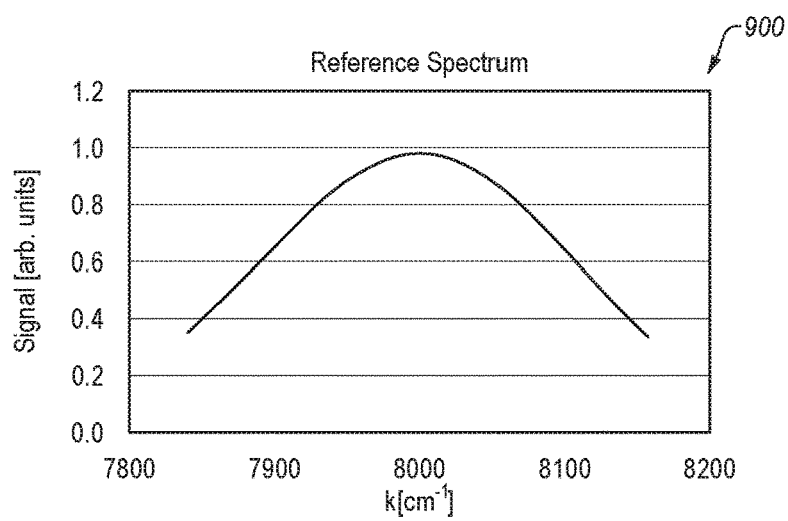
FIG. 9A illustrates a simulated spectrum that may be measured by a spectrometer of any of the example systems of FIGS. 1-4.
Figure 9B:
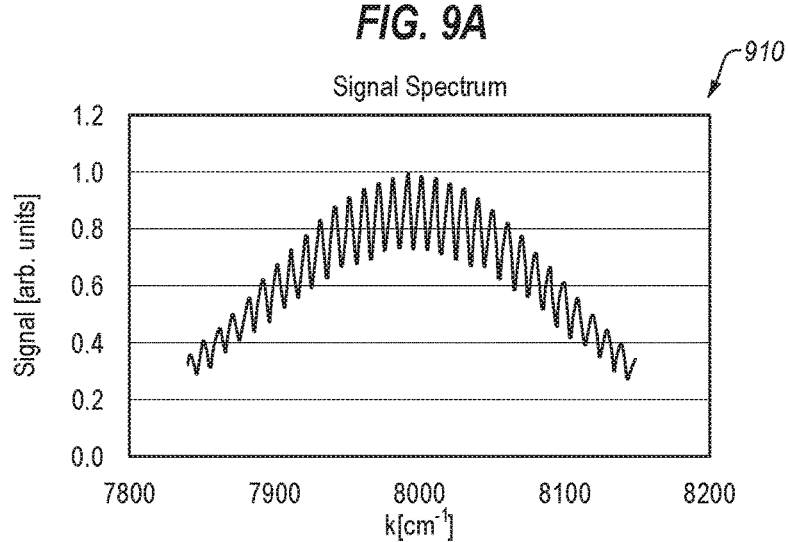
FIG. 9B illustrates a simulated spectrum that may be reflected from a slab of material.
Figure 9C:
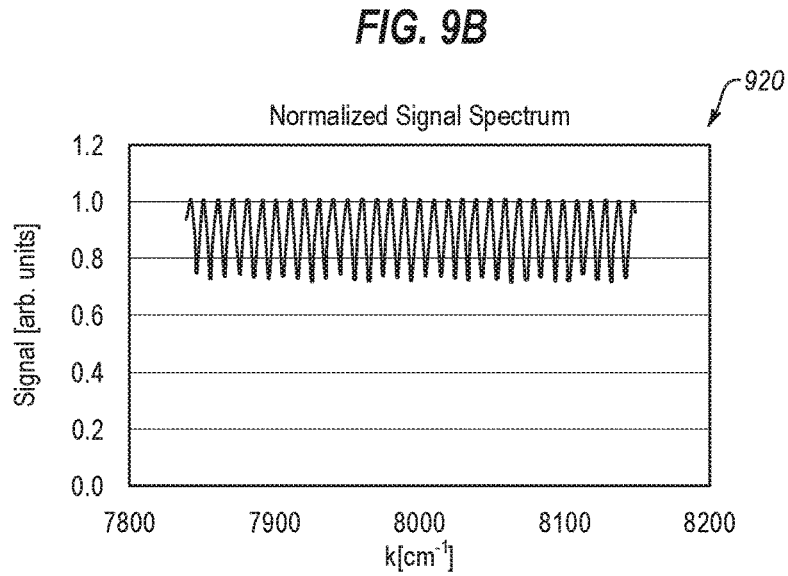
FIG. 9C illustrates a simulated normalized spectrum that may result from dividing the simulated spectrum of FIG. 9B using the simulated spectrum of FIG. 9A.

If the approximate thickness of the measured slab is known, then one etalon may be employed having a known and slightly larger thickness than the thickness of the slab of material 102 to measure the exact thickness 106 of the slab of material 102 using the system 100. For example, in this situation, the system 100 may be employed to measure the thickness 106 of the slab of material 102 by the following procedure:

1. Measuring the reference spectrum (as shown in FIG. 9A) of the broadband light source 116 by placing a mirror in place of the slab of material 102 using the system 100 in which the etalon filter 120 is temporarily removed, or in which the slab of material 102 is replaced by a very thick etalon filter having an optical thickness much greater than the optical thickness 106 of the measured slab of material 102.
2. Measuring the signal spectrum (as shown in FIG. 9B) of the light reflected from the slab of material 102 having a known refractive index n, and passing through the etalon filter 120 having a known thickness which is known to be slightly larger than the thickness 106 of the measured slab of material 102.
3. Calculating a normalized spectrum (as shown in FIG. 9C) by dividing the signal spectrum by the reference spectrum.
4. Calculating the frequency $\Omega$ of observed oscillations in the normalized spectrum.
5. Calculating the thickness 106 of the slab of material 102 using Equation 34.

The frequency calculation using a normalized signal in step 3 in the above procedure can be performed using one of many standard methods of signal processing including, but not limited to, Fourier transform methods, fitting oscillating model function methods, and investigating position of the maxima and minima of the oscillations shown in FIG. 9C.

Similarly, if the approximate thickness of the measured slab of material 102 is known, then one etalon having a known and slightly smaller thickness than the thickness 106 of the slab of material 102 may be employed to measure the exact thickness 106 of the slab of material 102 using system 100. For example, in this situation, the system 100 may be employed to measure the thickness 106 of the slab of material 102 by the following procedure:

1. Measuring the reference spectrum (as shown in FIG. 9A) of the broadband light source 116 by placing a mirror in place of the slab of material 102 using the system 100 in which the etalon filter 120 is temporarily removed, or in which the slab of material 102 is replaced by a very thick etalon filter having an optical thickness much greater than the optical thickness 106 of the measured slab of material 102.
2. Measuring the signal spectrum (as shown in FIG. 9B) of the light reflected from the slab of material 102 having a known refractive index n, and passing through the etalon filter 120 having a known thickness which is known to be slightly smaller than the thickness 106 of the measured slab of material 102.
3. Calculating a normalized spectrum by dividing the signal spectrum by the reference spectrum as shown in FIG. 13C.

4. Calculating the frequency Ω of observed oscillations in the normalized spectrum.
5. Calculating the thickness 106 of the slab of material 102 using Equation 35.

Measurements using N etalons having different optical thicknesses may be performed using the following steps, where N=2, 3, . . . :

1. Measuring the reference spectrum (as shown in FIG. 9A) of the broadband light source 116 by placing a mirror in place of the slab of material 102 using the system 100 in which the etalon filter 120 is temporarily removed, or in which the slab of material 102 is replaced by very thick etalon filter of having an optical thickness much greater than the optical thickness 106 of the measured slab of material 102.
2. Measuring the signal spectra (as shown in FIG. 9B) of the light reflected from the slab of material 102 having a known refractive index n, and passing through each of the employed etalons i=1,2.
3. Calculating a normalized spectra (as shown in FIG. 9C) by dividing the signal spectra by the reference spectrum.
4. Calculating the frequency Ω of observed oscillations in the normalized spectrum.

Finding an approximate solution d of the (overdetermined) system of equations following from Equation (33) using the following Equation:

$$\Omega_i = \frac{2\pi|(n_{ref,i}d_{ref,i} - nd)|}{c} \quad (36)$$

where i=1, . . . , N, and $n_{ref,i}$ is a refractive index of etalon having index I and $d_{ref,i}$ is the thickness of the etalon having an index i.

Figure 2:
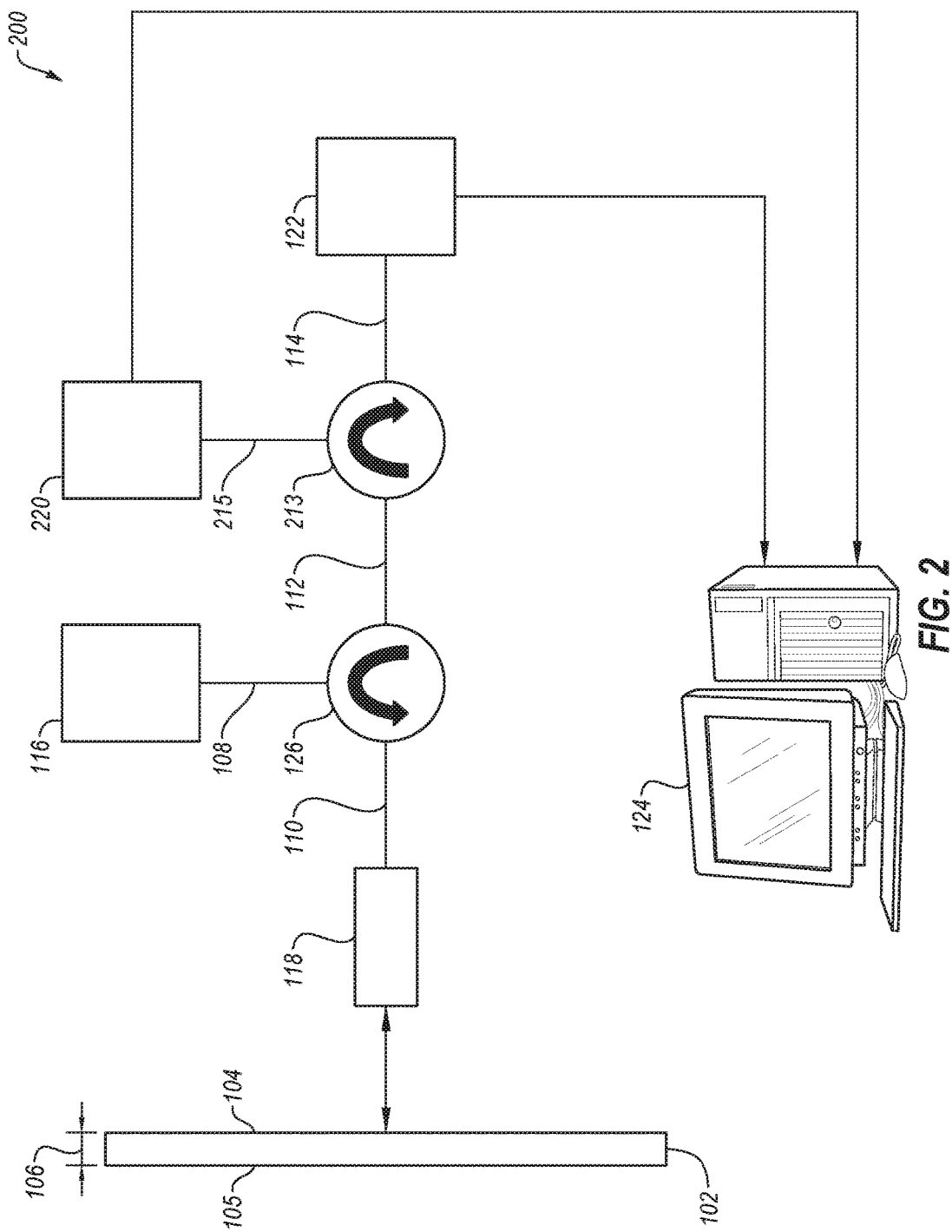
FIG. 2 illustrates a second example system for inspecting a slab of material.

FIG. 2 illustrates a second example system 200 for inspecting a slab of material, arranged in accordance with at least some embodiments described in this disclosure. Since the system 200 is similar in many respects to the system 100 of FIG. 1, only the differences between the system 200 and the system 100 will be discussed herein.

In additional to elements in common with the system 100, the system 200 may include a second directional element 213, an etalon filter 220, and a single mode optical fiber 215, which may be a polarization maintaining optical fiber in some embodiments.

The second directional element 213 may be configured to receive the light from the directional element 126 over the optical fiber 112 and direct the light to the etalon filter 220 over the optical fiber 215. The etalon filter 220 may be configured similarly to the etalon filter 120 of FIG. 1, except that the etalon filter 220 may be configured to receive the light from the second directional element 213 over the optical fiber 215 after the light has been reflected from the slab of material 102 and direct the light back to the second directional element 213 over the optical fiber 215. The spectrometer 122 of the system 200 may then be configured to receive the light from the second directional element 213 over the optical fiber 114.

Figure 3:
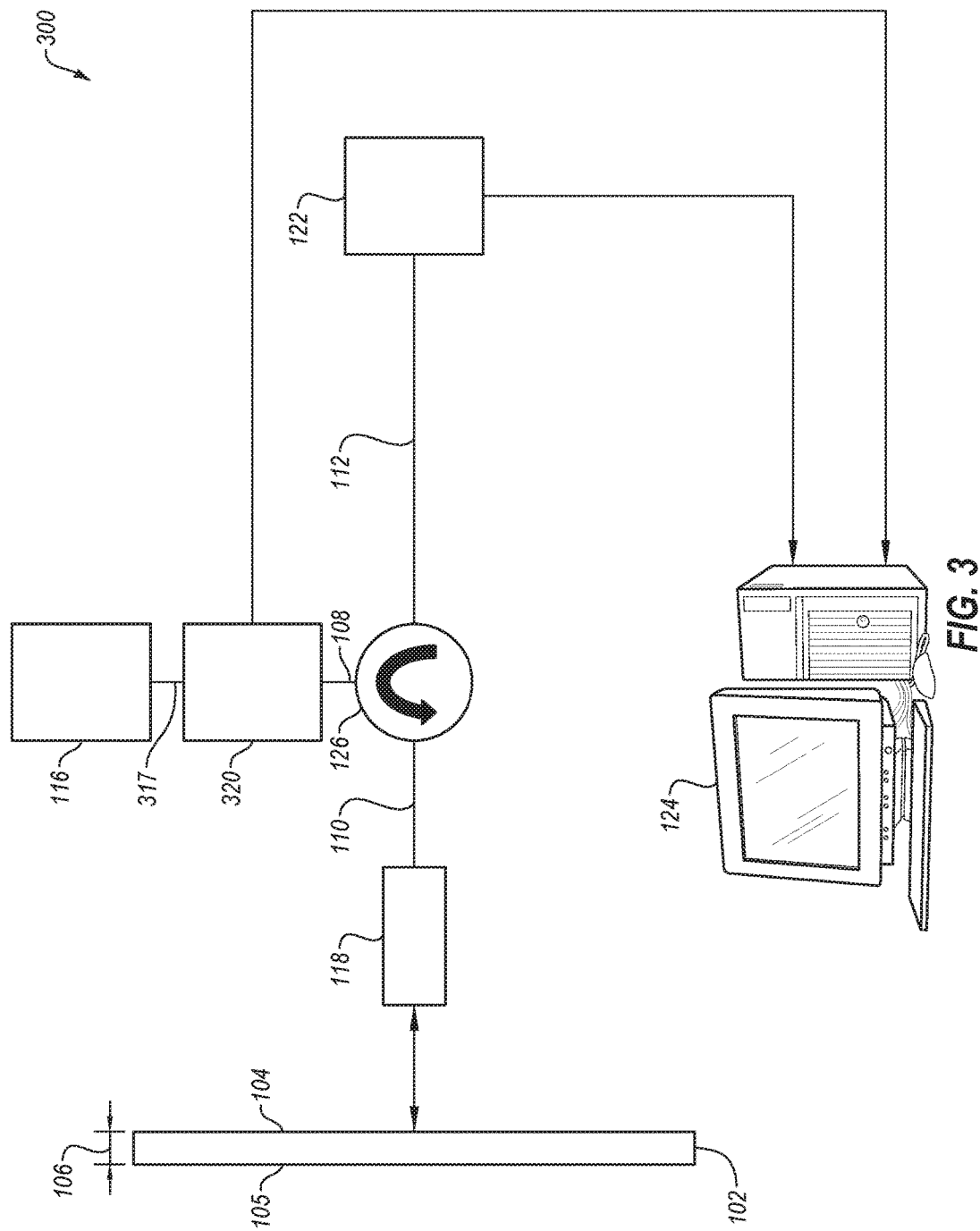
FIG. 3 illustrates a third example system for inspecting a slab of material.

FIG. 3 illustrates a third example system 300 for inspecting a slab of material, arranged in accordance with at least some embodiments described in this disclosure. Since the system 300 is similar in many respects to the system 100 of FIG. 1, only the differences between the system 300 and the system 100 be discussed herein.

In additional to elements in common with the system 100, the system 300 may include a single mode optical fiber 317 (which may be a polarization maintaining optical fiber in some embodiments) and an etalon filter 320.

The etalon filter 320 may be configured similarly to the etalon filter 120 of FIG. 1, except that the etalon filter 320 may be configured to receive the light (which may be linearly polarized in some embodiment) from the broadband light source 116 over the optical fiber 317 before the light is directed toward the slab of material 102 and then, after filtering the light, direct the light over the optical fiber 108 to the directional element 126. Then, after the light has been reflected from the slab of material 102, the spectrometer 122 may be configured to receive the light from the directional element 126 over the optical fiber 112.

Figure 4:
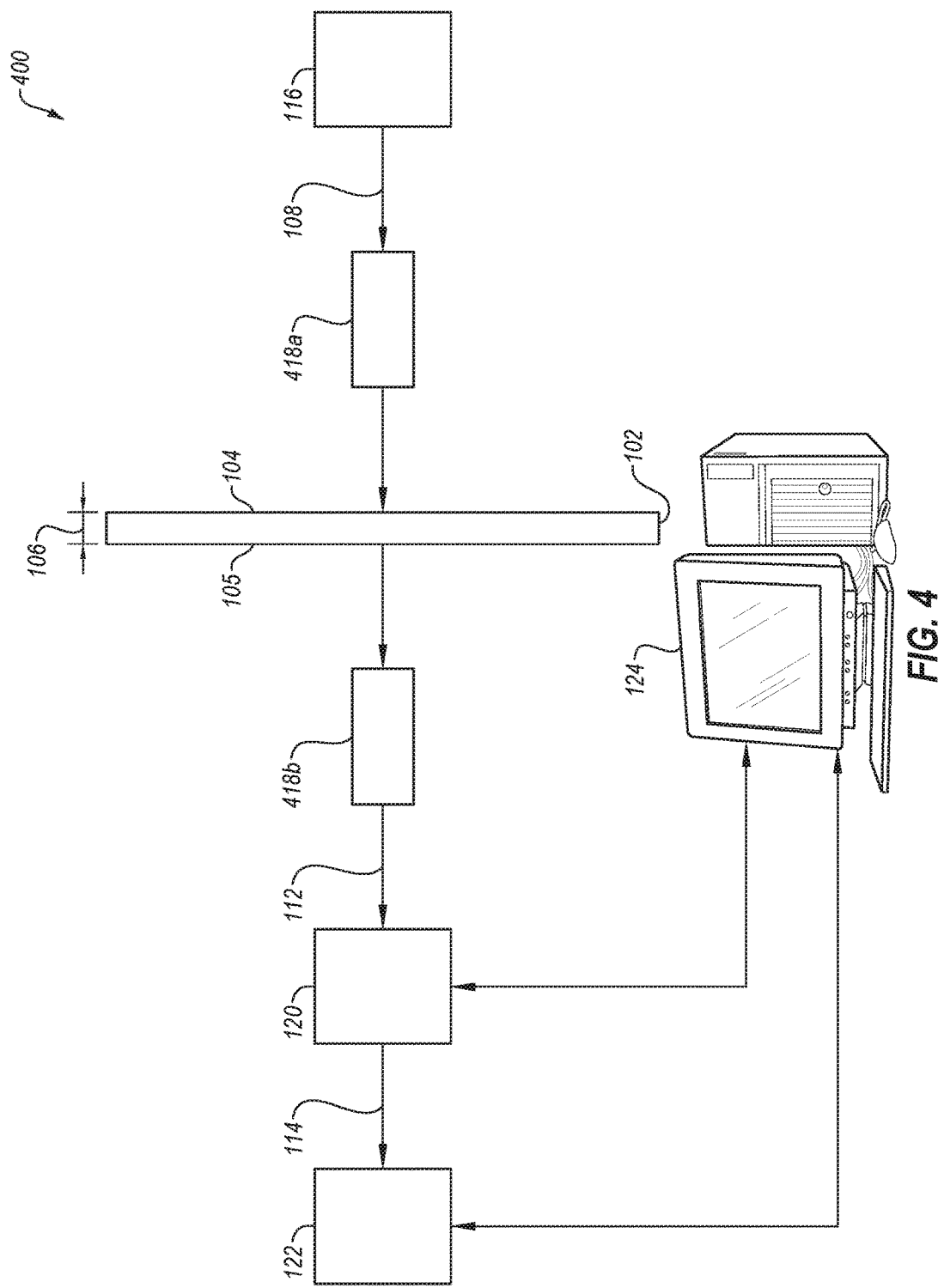
FIG. 4 illustrates a fourth example system for inspecting a slab of material.

FIG. 4 illustrates a fourth example system 400 for inspecting a slab of material, arranged in accordance with at least some embodiments described in this disclosure. Since the system 400 is similar in many respects to the system 100 of FIG. 1, only the differences between the system 400 and the system 100 be discussed herein.

In additional to elements in common with the system 100, the system 400 may include a first beam-forming assembly 418a and a second beam-forming assembly 418b.

The beam-forming assembly 418a may be similar to the beam-forming assembly 118 of FIG. 1 except that the beam-forming assembly is not configured to receive the light reflected back from the slab of material 102. Instead, the light directed from the beam-forming assembly 418a is transmitted through the slab of material 102 toward the second beam-forming assembly 418b via a first half wave plate 119a (or any other polarization rotator) the controls the plane of polarization of the light. The second beam-forming assembly 418b may be configured to receive the light transmitted through the slab of material 102 via a second half wave plate 119b (or any other polarization rotator), and direct the light to the etalon-filter 120 over the optical fiber 112. The etalon filter 120 may then be configured to receive the light from the second beam-forming assembly 118b over the optical fiber 112 after the light has been transmitted through the slab of material. In some embodiments, the system 400 may omit the half wave plates 119.

The systems 200, 300, and 400 of FIGS. 2, 3, and 4, respectively, may operate according to very similar principles. For example, since all components of the optical systems may be linear in light intensity, the ordering of the reference etalon (the etalon filter) and the sample (the slab of material) does not affect the signal produced by the system. Therefore, the systems 200 and 300 may produce substantially the same signal. The main difference between the systems 200 and 300 is use of a reference etalon operating in the transitive mode and the reflective mode, respectively. A similar analysis may be performed using either system, leading to Equations (34) and (35).

Figure 5A:
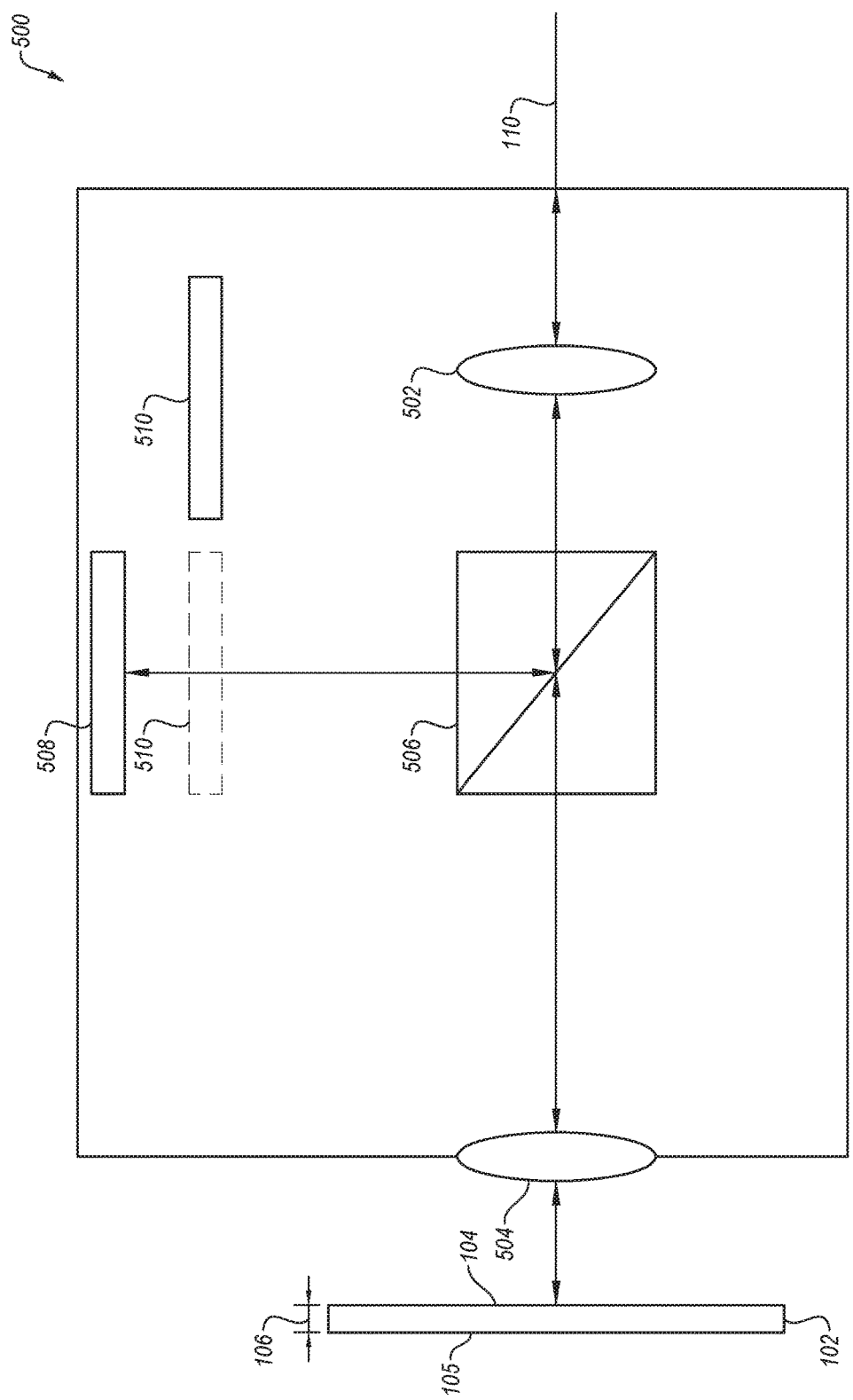
FIG. 5A illustrates an example beam-forming assembly that may be employed in the systems of FIGS. 1-4.

FIG. 5A illustrates an example beam-forming assembly 500, arranged in accordance with at least some embodiments described in this disclosure. The beam-forming assembly 500 may be employed as the beam-forming assembly 118 in the system 100 of FIG. 1, in the system 200 of FIG. 2, and in the system 300 of FIG. 3. The beam-forming assembly 500 may include lenses 502 and 504. The beam-forming assembly 500 may also optionally include a beam splitter 506 and a reflector 508. The lens 502 may be configured to receiving the light over the optical fiber 110 and collimate and direct the light toward the beam splitter 506. The beam splitter 506 may be configured to split the light from the lens 502 into first and second portions, direct the first portion of the light toward the lens 504, and direct the second portion of the light onto a reflector 508. The lens 504 may be configured to receive the first portion of the light from the beam splitter 506, direct the first portion of the light toward the slab of material 102, and direct the first portion of the light after being reflected from the slab of material 102 back toward the beam splitter 506. Further, the reflector 508 may be configured to receive the second portion of the light from the beam splitter 506 and reflect the second portion of the light back toward the beam splitter 506. The beam splitter 506 may be further configured to combine the first portion of the light after being reflected from the slab of material 102 and the second portion of the light after being reflected from the reflector 508, and then direct the combined light toward the lens 502. Finally, the lens 502 may be configured to receive the combined light and direct the combined light over the optical fiber 110.

The reflector 508 may be implemented, among other ways, as a mirror, or corner cube retro-reflector. It may be important to maintain a well-controlled distance between beam splitter 506 and reflector 508. In some circumstances a change of temperature may result in change in the distance between the beam splitter 506 and the reflector 508. To reduce the likelihood of a change in temperature from changing the distance between the beam splitter 506 and the reflector 508, in some embodiments, the entire beam-forming assembly 500 may be manufactured from the materials having small coefficient of thermal expansion such as, for example, Invar.

Figure 5B:
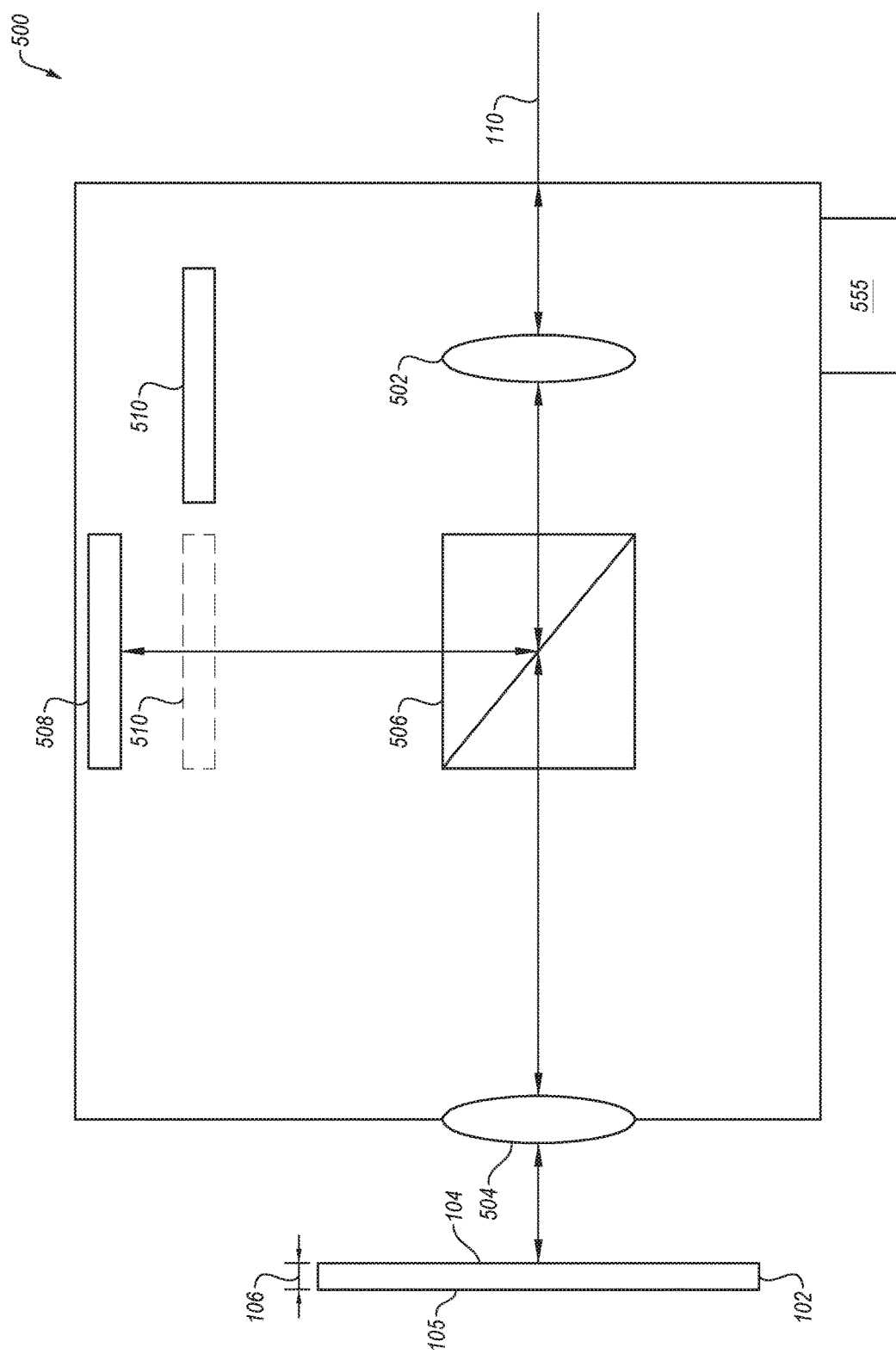
FIG. 5B illustrates an example beam-forming assembly that may be employed in the systems of FIGS. 1-4.

Additionally or alternatively, beam-forming assembly 500 may be maintained at a constant temperature or close to a constant temperature via of a temperature controller 555. FIG. 5B illustrates an example beam-forming assembly 500, arranged in accordance with at least some embodiments described in this disclosure. The temperature controller 555 may include a temperature sensor, a heater, and feedback electronics configured to assure that temperature of the beam-forming assembly 500 remains independent on the environment temperature. In some cases temperature controller 555 may also include a mechanism to provide cooling, such as, for example, a thermoelectric cooler.

The beam-forming assembly 500 may be employed to gauge the optical path difference (OPD) between the first portion of the light and the second portion of the light, which can be used to measure the distance between the front surface 104 of the slab of material 102 and the lens 504.

The topography of the front surface 104 of the slab of material 102 may be determined by placing a slab of material 102 on an XY motion stage perpendicular to the light beam impinging the front surface 104 of the slab of material 102, with the front surface 104 being parallel to the motion of the XY motion stage, and by collecting a data set comprising the data set on a large number M comprising the $x_j$ and $y_j$ coordinates of the point where the beam is impinging the front surface 104 of the slab of material 102 and the distance between stationary lens 504 and the front surface 104 of the slab of material 102 $z_j$, where j=1 ... M. The set of points ($x_j$, $y_j$, $z_j$) can then be used to construct a three dimensional map of the front surface 104 of the slab of material 102. A similar procedure may be performed to determine the topography of the back surface 105 of the slab of material 102.

As noted above, although the beam splitter 506 and the reflector 508 may be beneficial in some embodiments of the beam-forming assembly 500, it is understood that in other embodiments the beam-forming assembly may instead omit the beam splitter 506 and the reflector 508. For example, the beam-forming assembly 500 may be employed as the beam-forming assembly 118a and as the beam-forming assembly 118b in the system 400 of FIG. 4 and since the light only passes through the beam assemblies 118a and 118b in a single direction in the system 400, the beam splitter 506 and the reflector 508 may be omitted.

The beam directed towards the reflector 508 may be blocked by beam shutter 510 to avoid extra interference, such as in measurement modes where the usage of the reflector 508 is not required. The beam shutter 510 may be operated manually or may be computer controlled.

FIG. 6A illustrates an example etalon filter 600, arranged in accordance with at least some embodiments described in this disclosure. The etalon filter 600 may be employed as the etalon filter 120 in the systems 100 and 400 of FIGS. 1 and 4, respectively, and as the etalon filter 320 in the system 300 of FIG. 3.

The etalon filter 600 may include a first beam collimator 602, an etalon 604, and a second beam collimator 606. The first beam collimator 602 may be connected to the optical fiber 112 and the second beam collimator 606 may be connected to the optical fiber 114. The first beam collimator 602 may be configured to receive light from the optical fiber 112, collimate the light into a beam, and direct the beam toward the etalon 604.

FIG. 6B illustrates an etalon operating at a Brewster-angle in FIG. 6A. The etalon 604 is positioned at a 'Brewster angle' with respect to the collimated light from collimator 602 to reduce or eliminate reflection from the front surface of the etalon 604. The second beam collimator 606 may be configured to collect the beam that was transmitted through the etalon 604 and direct it into the optical fiber 114.

FIG. 7A illustrates an example etalon filter 700, arranged in accordance with at least some embodiments described in this disclosure. The etalon filter 700 may be employed as the etalon filter 220 in the system 200 of FIG. 2.

The etalon filter 700 may include a beam collimator 702 and an etalon 704. The beam collimator 702 may be connected to the optical fiber 112. The beam collimator 702 may be configured to receive light from the optical fiber 112, collimate the light into a beam, and direct the beam toward the etalon 704.

FIG. 7B illustrates an etalon operating at a Brewster-angle in FIG. 7A. The etalon 704 is positioned at a 'Brewster angle' with respect to the collimated light from collimator 702 to reduce or eliminate any reflection from the front surface of the etalon 704. The beam collimator 702 may also be configured to collect the beam that was reflected from the etalon 704 and direct it into the optical fiber 112.

Figure 8:
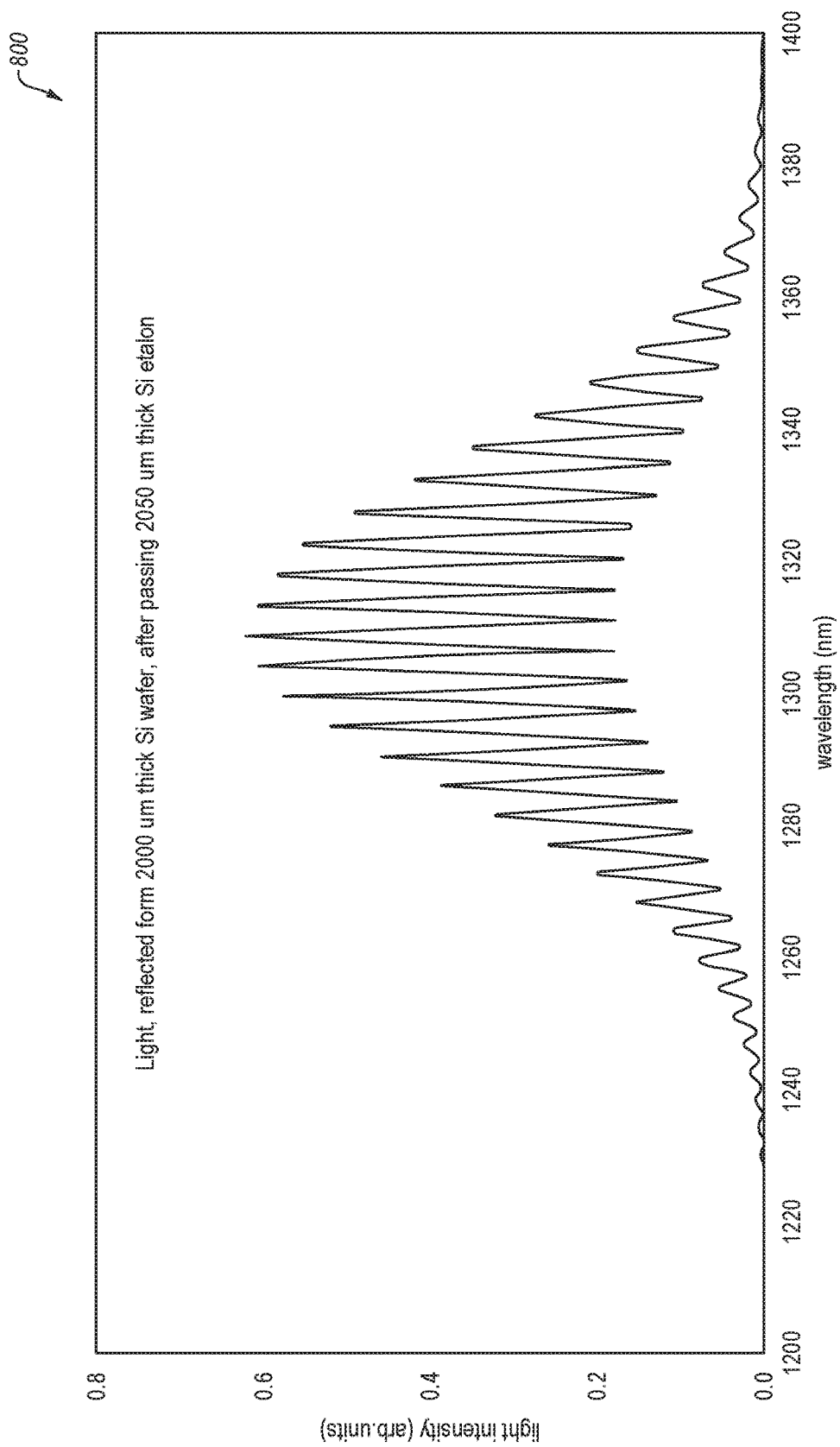
FIG. 8 illustrates a simulated spectrum that may be obtained using any of the example systems of FIGS. 1-4.

FIG. 8 illustrates a simulated spectrum 800 that may be obtained using any of the example systems of FIGS. 1-4. In particular, the spectrum 800 may be obtained by the spectrometer 122 of any of the systems of FIGS. 1-4 after the light has been reflected from or transmitted through the slab of material 102, where the slab of material is a 2000 um thick sapphire plate acting as a wafer carrier, and the etalon-filter is a 2050 um thick Si etalon.

FIG. 9A illustrates a simulated spectrum 900 that may be measured by a spectrometer of any of the example systems of FIGS. 1-4, FIG. 9B illustrates a simulated spectrum 910 that may be reflected from a slab of material, and FIG. 9C illustrates a simulated normalized spectrum 920 that may result from dividing the simulated spectrum 910 using the simulated spectrum 900. In particular, the simulated spectrum 900 is of a linearly polarized light source having a bandwidth half width half maximum 25 nm and centered at 1250 nm, as measured by a spectrometer having a bandwidth of 0.2 nm. The simulated spectrum 910 is reflected from a slab of material having a thickness of 0.6 mm, a refractive index of 3.5, and a reflection coefficient of each surface of 0.5, after having passed through an etalon filter having a thickness of 0.74 mm, a refractive index of 3.5, and a reflection coefficient of each surface of 0.5.

Figure 10:
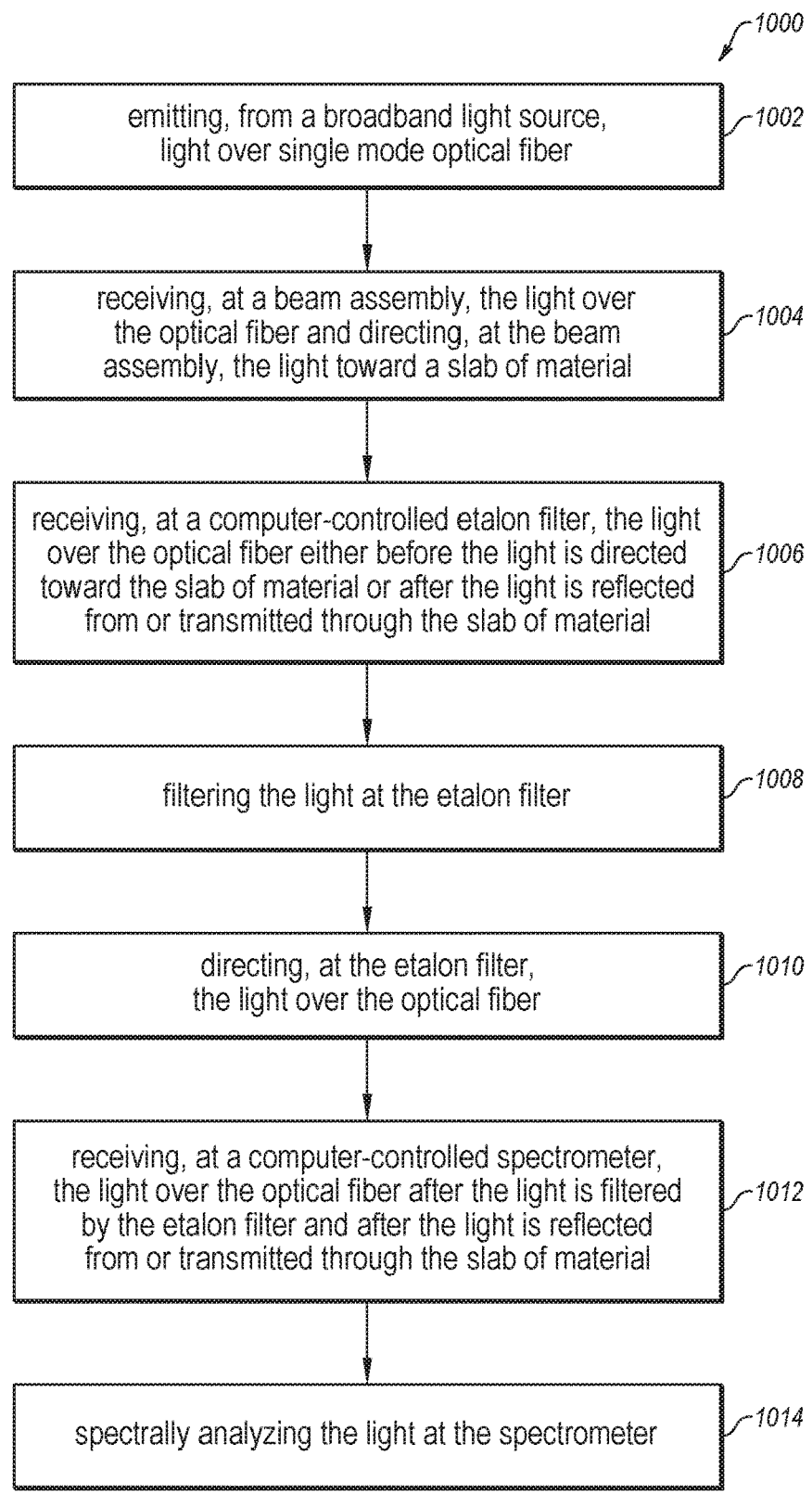
FIG. 10 is a flowchart of an example method for inspecting a slab of material.

FIG. 10 is a flowchart of an example method 1000 for inspecting a slab of material, arranged in accordance with at least some embodiments described in this disclosure. The method 1000 may be implemented, in some embodiments, by a system, such as any of the systems 100, 200, 300, and 400 of FIGS. 1, 2, 3, and 4, respectively. Although illustrated as discrete blocks, various blocks may be divided into additional blocks, combined into fewer blocks, or eliminated, depending on the desired implementation.

In some embodiments, block 1002 may include emitting, from a broadband light source, light over single mode optical fiber. Additionally or alternatively, block 1002 may include emitting, from a linearly polarized broadband light source, light over a polarization maintaining single mode optical-fiber. The plane of polarization or a direction of polarization of light from the linearly-polarized source may be pre-defined.

Block 1004 may include receiving, at a beam-forming assembly, the light over the optical fiber and directing, at the beam-forming assembly, the light toward a slab of material. In some embodiments, the block 1004 may further include splitting, at the beam-forming assembly, the light into first and second portions after receiving, at the beam-forming assembly, the light over the optical fiber, directing, at the beam-forming assembly, the first portion of the light toward the slab of material, directing, at the beam-forming assembly, the second portion of the light onto a reflector, combining, at the beam-forming assembly, the first portion of the light after being reflected from the slab of material and the second portion of the light after being reflected from the reflector, and directing, at the beam-forming assembly, the combined light over the optical fiber.

In some embodiments, block 1004 may include controlling, by a half-wave plate or any other polarization-rotator, polarization of the light directed to the slab of material from the beam-assembly. More specifically, the half-wave plate controls the plane of polarization of the light directed to the slab of material by rotating the plane of polarization through a pre-defined angle.

Block 1006 may include receiving, at a computer-controlled etalon filter, the light over the optical fiber either before the light is directed toward the slab of material or after the light has been reflected from or transmitted through the slab of material. The etalon within the etalon filter may be placed at a Brewster-angle with respect to the incoming or incident light to reduce reflection from a front-surface thereof.

Block 1008 may include filtering the light at the etalon-filter.

Block 1010 may include directing, at the etalon filter, the light over the optical fiber.

Block 1012 may include receiving, at a computer-controlled spectrometer, the light over the optical fiber after the light has been filtered by the etalon-filter and after the light has been reflected from or transmitted through the slab of material. The computer-controlled spectrometer may include the dispersive element as a grating, which may be positioned to facilitate a pre-determined angle between at least one groove thereof and the plane of polarization of the light received over the optical-fiber. Additionally or alternatively, the computer-controlled spectrometer may include the dispersive element as a prism, wherein the prism is positioned at a Brewster-angle with respect to an incident light (e.g., the polarized light) to reduce reflection from a first-surface thereof.

Block 1014 may include spectrally analyzing the light at the spectrometer. In some embodiments, the block 1014 may include determining a topography of one or more surfaces of the slab of material and/or determining a thickness of the slab of material. In an example, the spectrometer may be provided with etalon for the purposes of rendering interference that is captured as a part of spectral-analysis.

One skilled in the art will appreciate that, for this and other methods disclosed in this disclosure, the functions performed in the methods may be implemented in differing order. Furthermore, the outlined operations are only provided as examples, and some of the operations may be optional, combined into fewer operations, or expanded into additional operations without detracting from the essence of the disclosed embodiments.

For example, in some embodiments, blocks 1008, 1010, and 1012 may be performed prior to the block 1004, such as when the method 1000 is performed by the system 300 of FIG. 3.

Further, in some embodiments, the method 1000 may further include receiving, at a directional element, the light from the broadband light source over the optical fiber and directing, at the directional element, the light to the beam-forming assembly over the optical fiber, receiving, at the beam-forming assembly, the light reflected from the slab of material and directing, at the beam-forming assembly, the light back to the directional element over the optical fiber, where the light received at the etalon filter is received from the directional element after the light has been reflected from the slab of material and where the light received at the spectrometer is received from the etalon filter, such as when the method 1000 is performed by the system 100 of FIG. 1.

Further, in some embodiments, the method 1000 may further include receiving, at a directional element, the polarized light from the linearly polarized broadband light source over the polarization maintaining optical fiber and directing, at the directional element, the light to the beam-forming assembly over the optical fiber, controlling, by the half wave plate or any other polarization rotator, the polarization of light impinging the slab of material, receiving, at the beam-forming assembly, the light reflected from the slab of material and directing, at the beam-forming assembly, the light back to the directional element over the optical fiber, where the light received at the etalon filter is received from the directional element after the light has been reflected from the slab of material and where the light received at the spectrometer is received from the etalon filter, such as when the method 1000 is performed by the system 100 of FIG. 1.

Alternatively, in some embodiments, the method 1000 may further include receiving, at a first directional element, the light from the broadband light source over the optical fiber and directing, at the first directional element, the light to the beam-forming assembly over the optical fiber, receiving, at the beam-forming assembly, the light reflected from the slab of material and directing, at the beam-forming assembly, the light back to the first directional element over the optical fiber, and receiving, at a second directional element, the light from the first directional element over the optical fiber and directing, at the second directional element, the light to the etalon filter over the optical fiber, where the light received at the etalon filter is received from the second directional element after the light has been reflected from the slab of material. In these embodiments, the method 1000 may further include directing, at the etalon filter, the light back to the second directional element over the optical fiber, where the light received at the spectrometer is received from the second directional element, such as when the method 1000 is performed by the system 200 of FIG. 2.

Alternatively, in some embodiments, the method 1000 may further include receiving, at a first directional element, the light from the linearly polarized broadband light source over the polarization maintaining optical fiber and directing, at the first directional element, the light to the beam-forming assembly over the optical fiber, controlling, by the half wave plate or any other polarization rotator, the polarization of light impinging the slab of material, receiving, at the beam-forming assembly, the light reflected from the slab of material and directing, at the beam-forming assembly, the light back to the first directional element over the optical fiber, and receiving, at a second directional element, the light from the first directional element over the optical fiber and directing, at the second directional element, the light to the etalon filter over the optical fiber, where the light received at the etalon filter is received from the second directional element after the light has been reflected from the slab of material. In these embodiments, the method 1000 may further include directing, at the etalon filter, the light back to the second directional element over the optical fiber, where the light received at the spectrometer is received from the second directional element, such as when the method 1000 is performed by the system 200 of FIG. 2.

Alternatively, in some embodiments, the method 1000 may further include receiving, at a directional element, the light from the etalon filter over the optical fiber and directing, at the directional element, the light to the beam-forming assembly over the optical fiber, where the light received at the etalon filter is received from the broadband light source before the light is directed toward the slab of material. In these embodiments, the method 1000 may further include receiving, at the beam-forming assembly, the light reflected from the slab of material and directing, at the beam-forming assembly, the light back to the directional element over the optical fiber, where the light received at the spectrometer is received from the directional element, such as when the method 1000 is performed by the system 300 of FIG. 3.

In these or other embodiments, the method 1000 may further include receiving, at a directional element, the light from the etalon filter over the optical fiber and directing, at the directional element, the light to the beam-forming assembly over the optical fiber, where the light received at the etalon filter is received from the linearly polarized broadband light source before the light is directed toward the slab of material. In these embodiments, the method 1000 may further include controlling, by the half wave plate or any other polarization rotator, the polarization of light impinging the slab of material, receiving, at the beam-forming assembly, the light reflected from the slab of material and directing, at the beam-forming assembly, the light back to the directional element over the optical fiber, where the light received at the spectrometer is received from the directional element, such as when the method 1000 is performed by the system 300 of FIG. 3.

Alternatively, in some embodiments, the method 1000 may further include receiving, at a second beam-forming assembly, the light transmitted through the slab of material and directing, at the second beam-forming assembly, the light to the etalon filter over the optical fiber, where the light received at the etalon filter is received from the second beam-forming assembly after the light has been transmitted through the slab of material, and where the light received at the spectrometer is received from the etalon filter, such as when the method 1000 is performed by the system 400 of FIG. 4.

Terms used in this disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description of embodiments, claims, or drawings, should be understood to contemplate the possibilities of including one of the terms, either of the terms, or both terms. For example, the phrase "A or B" should be understood to include the possibilities of "A" or "B" or "A and B."

All examples and conditional language recited in this disclosure are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that various changes, substitutions, and alterations could be made hereto without departing from the spirit and scope of the present disclosure.

The invention claimed is:

1. A system for inspecting a slab of material, the system comprising:
   single mode optical fiber;
   a broadband light source configured to emit light with wavelengths in a range from 780 nanometers (nm) to 1800 nm over the optical fiber;
   a beam-forming assembly configured to receive the light over the optical fiber and direct the light toward a slab of material;

a computer-controlled etalon filter configured to receive the light over the optical fiber either before the light is directed toward the slab of material or after the light has been reflected from or transmitted through the slab of material, filter the light, and direct the light over the optical fiber; and a computer-controlled spectrometer configured to receive the light over the optical fiber after the light has been filtered by the etalon filter and after the light has been reflected from or transmitted through the slab of material and spectrally analyze the light.

2. The system of claim 1, wherein the broadband light source is configured to emit light with wavelengths in a range of 780 nm to 1000 nm.

3. The system of claim 1, wherein the broadband light source is configured to emit light with wavelengths in a range of 800 nm to 1000 nm.

4. The system of claim 3, wherein the computer-controlled spectrometer comprises a silicon-based detector.

5. The system of claim 1, wherein the broadband light source is configured to emit light with wavelengths in a range of 1100 nm to 1800 nm.

6. The system of claim 1, wherein the broadband light source is configured to emit light with wavelengths in a range of 1200 nm to 1500 nm.

7. The system of claim 6, wherein the computer-controlled spectrometer comprises an Indium Gallium Arsenide detector.

8. The system of claim 1, wherein the broadband light source comprises a Superluminescent Light Emitter Device.

9. The system of claim 1, wherein each of the single mode fiber, the beam-forming assembly, the computer-controlled etalon filter, and the computer-controlled spectrometer are configured to operate in the same wavelength range as the light emitted by the broadband light source.

10. A system for inspecting a slab of material, the system comprising: single mode optical fiber; a broadband light source configured to emit light over the optical fiber; a beam-forming assembly configured to: receive the light over the optical fiber; split the light, at a beam splitter, into first and second portions after receiving the light over the optical fiber; direct the first portion of the light toward the slab of material; direct the second portion of the light onto a reflector that is maintained at a substantially constant distance from the beam splitter; combine the first portion of the light after being reflected from the slab of material and the second portion of the light after being reflected from the reflector; and direct the combined light over the optical fiber; a computer-controlled etalon filter configured to receive the light over the optical fiber either before the light is directed toward the slab of material or after the light has been reflected from or transmitted through the slab of material, filter the light, and direct the light over the optical fiber; and a computer-controlled spectrometer configured to receive the light over the optical fiber after the light has been filtered by the etalon filter and after the light has been reflected from or transmitted through the slab of material and spectrally analyze the light.

11. The system of claim 9, wherein the beam-forming assembly is comprised of materials having a low coefficient of thermal expansion such that in response to an increase or decrease in a temperature of the system, the reflector is maintained at a substantially constant distance from the beam splitter.

12. The system of claim 10, wherein the beam-forming assembly is comprised of Invar.

13. The system of claim 9, further comprising a temperature controller that is configured to maintain the beam-forming assembly at a substantially constant temperature.

14. The system of claim 12, wherein the temperature controller comprises a temperature sensor, a heater, and feedback electronics.

15. The system of claim 12, wherein the temperature controller comprises a thermoelectric cooler.

* * * * *